United States Patent
Greener et al.

(10) Patent No.: US 9,096,558 B2
(45) Date of Patent: Aug. 4, 2015

(54) N-SULFONYLBENZAMIDE COMPOUNDS

(75) Inventors: Benjamin Scott Greener, Sandwich (GB); Brian Edward Marron, Durham, NC (US); David Simon Millan, Sandwich (GB); David James Rawson, Sandwich (GB); Robert Ian Storer, Sandwich (GB); Nigel Alan Swain, Sandwich (GB)

(73) Assignees: Pfizer Limited, Sandwich (GB); Icagen, Inc., Durham, NC (US)

( * ) Notice: Subject to any disclaimer, the term of this patent is extended or adjusted under 35 U.S.C. 154(b) by 139 days.

(21) Appl. No.: 13/808,633

(22) PCT Filed: Jul. 1, 2011

(86) PCT No.: PCT/IB2011/052920
§ 371 (c)(1),
(2), (4) Date: Jan. 7, 2013

(87) PCT Pub. No.: WO2012/004714
PCT Pub. Date: Jan. 12, 2012

(65) Prior Publication Data
US 2013/0109696 A1 May 2, 2013

Related U.S. Application Data

(60) Provisional application No. 61/362,919, filed on Jul. 9, 2010.

(51) Int. Cl.
| | |
|---|---|
| C07D 285/08 | (2006.01) |
| C07D 417/02 | (2006.01) |
| C07D 417/06 | (2006.01) |
| C07D 417/12 | (2006.01) |
| A61K 31/433 | (2006.01) |
| A61K 31/501 | (2006.01) |
| A61K 31/4439 | (2006.01) |
| C07D 285/135 | (2006.01) |
| C07D 401/12 | (2006.01) |
| A61K 45/06 | (2006.01) |

(52) U.S. Cl.
CPC .......... *C07D 285/135* (2013.01); *A61K 31/433* (2013.01); *A61K 31/4439* (2013.01); *A61K 31/501* (2013.01); *A61K 45/06* (2013.01); *C07D 285/08* (2013.01); *C07D 401/12* (2013.01); *C07D 417/12* (2013.01)

(58) Field of Classification Search
None
See application file for complete search history.

(56) References Cited

U.S. PATENT DOCUMENTS

| | | |
|---|---|---|
| 8,242,128 B2 | 8/2012 | Stahle |
| 2009/0143358 A1 | 6/2009 | Marron et al. |
| 2012/0010182 A1 | 1/2012 | Brown et al. |
| 2012/0010183 A1 | 1/2012 | Bell et al. |
| 2012/0010207 A1 | 1/2012 | Bell et al. |
| 2013/0109667 A1 | 5/2013 | Markworth et al. |
| 2013/0109701 A1 | 5/2013 | Brown et al. |
| 2013/0109708 A1 | 5/2013 | Brown et al. |
| 2013/0116285 A1 | 5/2013 | Bell et al. |

FOREIGN PATENT DOCUMENTS

| | | |
|---|---|---|
| EP | 0967201 A1 | 12/1999 |
| WO | 9910320 A1 | 3/1999 |
| WO | 0041505 A2 | 7/2000 |
| WO | 0105393 A2 | 1/2001 |
| WO | 02089785 A1 | 11/2002 |
| WO | 02089793 A1 | 11/2002 |
| WO | 02092585 A1 | 11/2002 |
| WO | 03022277 A1 | 3/2003 |
| WO | 2004037233 A2 | 5/2004 |
| WO | 2004043368 A2 | 5/2004 |
| WO | 2004043917 A1 | 5/2004 |
| WO | 2004043948 A1 | 5/2004 |
| WO | 2004084898 A1 | 10/2004 |
| WO | 2005000309 A2 | 1/2005 |
| WO | 2006120544 A1 | 11/2006 |

(Continued)

OTHER PUBLICATIONS

Obrecht, Daniel, et al., Regioselective Synthesis of Highly Substituted Aromatic Sulfides via Carbonyl-Alkyne Exchange Reaction, J. Org. Chem., 1999, pp. 6182-6189, vol. 64.
Basu, U.P., et al., Acridine Derivatives as Antimalarials. Part II. Journal of the Indian Chemical Society, 1939, pp. 100-106, vol. 16.
Das-Gupta, S. J., Acridine Derivatives as Antimalarials. Part IV, Journal of the Indian Chemical Society, 1939, pp. 364-368, vol. 16.
Silverman, Richard B., The Organic Chemistry of Drug Design and Drug Action, 2nd Ed. 2004, pp. 29-32—Elsevier, Burlington, MA.

*Primary Examiner* — Theodore R West
(74) *Attorney, Agent, or Firm* — J. Michael Dixon

(57) ABSTRACT

The invention relates to sulfonamide derivatives, to their use in medicine, to compositions containing them, to processes for their preparation and to intermediates used in such processes. More particularly the invention relates to new sulfonamide Nav1.7 inhibitors of formula (I) or pharmaceutically acceptable salts thereof, wherein X, Y¹, Y², Z, R¹, R² and R³ are as defined in the description. Nav 1.7 inhibitors are potentially useful in the treatment of a wide range of disorders, particularly pain.

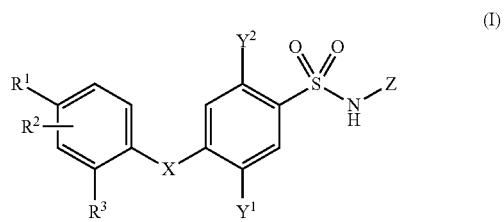

15 Claims, No Drawings

(56) References Cited

FOREIGN PATENT DOCUMENTS

| | | |
|---|---|---|
| WO | 2007033002 A1 | 3/2007 |
| WO | 2008008234 A1 | 1/2008 |
| WO | 2008069997 A1 | 6/2008 |
| WO | 2008075353 A1 | 6/2008 |
| WO | 2008079291 A2 | 7/2008 |
| WO | 2008092666 A1 | 8/2008 |
| WO | 2008118758 A1 | 10/2008 |
| WO | 2009086123 A1 | 7/2009 |
| WO | 2009086129 A1 | 7/2009 |
| WO | 2009086130 A1 | 7/2009 |
| WO | 2010059627 A1 | 5/2010 |
| WO | 2010079443 A1 | 7/2010 |

N-SULFONYLBENZAMIDE COMPOUNDS

CROSS REFERENCE

This application is the National Stage Application of International Patent Application No. PCT/IB2011/052920, filed Jul. 1, 2011, which claims priority to U.S. Provisional patent Application No. 61/362,919, filed on Jul. 9, 2010.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_v$x.x. The VGSC family has been phylogenetically divided into two subfamilies $Na_v$1.x (all but SCN6A) and $Na_v$2.x (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v$1.7 may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v$1.7 protein has been shown to accumulate in neuromas, particularly painful neuromas (Kretschmer et al., *Acta. Neurochir.* (*Wien*), 144(8): 803-10 (2002)). Gain of function mutations of $Na_v$1.7, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.*; 52(5):767-74 (2006). Further evidence of the role of Nav1.7 in pain is found in the phenotype of loss of function mutations of the SCN9A gene. Cox and colleagues (*Nature,* 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.*; 71(4): 311-9 (2007), Ahmad et al, *Hum Mol Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v$1.7 inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

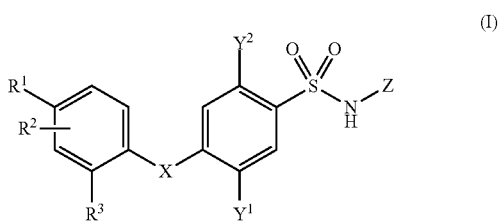

or a pharmaceutically acceptable salt thereof, wherein:

Z is a 'C-linked' 5- or 6-membered heteroaryl comprising (a) one or two nitrogen atoms or, when 5-membered, (b) one or two nitrogen atoms and one sulphur atom, said heteroaryl being optionally substituted on a ring carbon atom by F or Cl;

$Y^1$ is CN, F, Cl or $R^4$;

$Y^2$ is H or F;

X is $CH_2$ or S;

$R^1$ and $R^2$ are independently H, Cl, F, $R^5$, Ar or $Het^1$;

$R^3$ is H, F, $R^5$, Ar or $Het^1$;

$R^4$ is $(C_1-C_4)$alkyl optionally substituted by one to three F;

$R^5$ is $(C_1-C_4)$alkyl, optionally substituted by one to three F; or $(C_1-C_4)$alkyloxy, optionally substituted by one to three F;

Ar is phenyl optionally substituted by one to three atoms or groups selected from Cl, F or $R^5$;

$Het^1$ is a 'C-linked' 5- or 6-membered heteroaryl group comprising one or two nitrogen atoms, being optionally substituted by one to three substituents selected from A or B;

A is attached to a $Het^1$ ring carbon and is selected from $Het^2$, $NH_2$ and $R^4$;

B is attached to a $Het^1$ ring nitrogen and is selected from 'C-linked' $Het^2$ and $R^4$; and $Het^2$ is a 'C-linked' 3- to 8-membered saturated heterocyclic group comprising one or two ring nitrogen atoms, or (b) one oxygen atom and one or two nitrogen atoms, said heterocyclic group being optionally substituted by $R^4$.

Described below are a number of embodiments (E) of this first aspect of the invention, where for convenience E1 is identical thereto.

E1 A compound of formula (I) as defined above or a pharmaceutically acceptable salt thereof.

E2 A compound according to E1 wherein X is S.

E3 A compound according to E1 wherein X is $CH_2$.

E4 A compound according to any of E1 to E3 wherein Z is either (a) a 'C-linked' 5-membered heteroaryl group containing two nitrogen atoms and one sulphur atom, or (b) a 'C-linked' 6-membered heteroaryl group containing two nitrogen atoms.

E5 A compound according to any of E1 to E4 wherein Z is 'C-linked' thiadiazolyl or 'C-linked' a pyrimidinyl.

E6 A compound according to any of E1 to E5 wherein Z is 'C-linked' thiadiazolyl, such as 'C-linked' 1,3,4-thiadiazolyl.

E7 A compound according to any of E1 to E6 wherein $Y^1$ is Cl and $Y^2$ is F.

E8 A compound according to any of E1 to E7 wherein $Y^1$ is CN and $Y^2$ is H.

E9 A compound according to any of E1 to E8 wherein $R^1$ and $R^2$ are independently H, F, Cl or $R^5$.

E10 A compound according to any of E1 to E9 wherein $R^1$ and $R^2$ are independently H, F, $CF_3$ or $OCH_3$.

E11 A compound according to any of E1 to E9 wherein $R^1$ is H, F, $CF_3$ or $OCH_3$; and $R^2$ is H.

E12 A compound according to any of E1 to E11 wherein $R^3$ is H, F, $R^5$ or $Het^1$.

E13 A compound according to any of E1 to E12 wherein $R^3$ is H; F; $(C_1-C_4)$alkyl, optionally substituted by one to three halo; $(C_1-C_4)$alkyloxy, such as methoxy; or a 'C-linked' 6-membered heteroaryl group comprising one or two nitrogen atoms, optionally substituted on a carbon atom by $NH_2$.

E14 A compound according to any of E1 to E13 wherein $R^3$ is H; F; $(C_1-C_2)$alkyl, optionally substituted by one to three halo; $(C_1-C_2)$alkyloxy, such as methoxy; or a 'C-linked' 6-membered heteroaryl group comprising one or two nitrogen atoms.

E15 A compound according to E1 selected from:

5-chloro-2-fluoro-N-1,3,4-thiadiazol-2-yl-4-{[3-(trifluoromethyl)phenyl]thio}benzenesulfonamide;

5-chloro-2-fluoro-4-[(4-methoxyphenyl)thio]-N-1,3,4-thiadiazol-2-ylbenzenesulfonamide;

3-cyano-4-[(3-methoxyphenyl)thio]-N-1,2,4-thiadiazol-5-ylbenzenesulfonamide;

5-chloro-2-fluoro-4-[(3-methoxyphenyl)thio]-N-1,3,4-thiadiazol-2-ylbenzenesulfonamide;

5-chloro-2-fluoro-N-1,3,4-thiadiazol-2-yl-4-{[2-(trifluoromethyl)phenyl]thio}benzenesulfonamide;

5-chloro-2-fluoro-4-[(3-fluorophenyl)thio]-N-1,3,4-thiadiazol-2-ylbenzenesulfonamide;

5-chloro-2-fluoro-4-[(2-fluorophenyl)thio]-N-1,3,4-thiadiazol-2-ylbenzenesulfonamide;

5-chloro-2-fluoro-4-[(2-methoxyphenyl)thio]-N-1,3,4-thiadiazol-2-ylbenzenesulfonamide;

5-chloro-4-[(3,4-difluorophenyl)thio]-2-fluoro-N-1,3,4-thiadiazol-2-ylbenzenesulfonamide;

5-chloro-2-fluoro-N-1,3,4-thiadiazol-2-yl-4-{[4-(trifluoromethyl)phenyl]thio}benzenesulfonamide;

3-cyano-4-[(4-methoxyphenyl)thio]-N-1,2,4-thiadiazol-5-ylbenzenesulfonamide;

3-cyano-4-[(2-methoxyphenyl)thio]-N-1,2,4-thiadiazol-5-ylbenzenesulfonamide;

3-cyano-N-1,2,4-thiadiazol-5-yl-4-{[3-(trifluoromethyl)phenyl]thio}benzenesulfonamide;

3-cyano-N-1,2,4-thiadiazol-5-yl-4-{[4-(trifluoromethyl)phenyl]thio}benzenesulfonamide;

3-cyano-4-[(2-fluorophenyl)thio]-N-1,2,4-thiadiazol-5-ylbenzenesulfonamide;

3-cyano-N-1,2,4-thiadiazol-5-yl-4-{[2-(trifluoromethyl)phenyl]thio}benzenesulfonamide;

3-cyano-4-[(3,4-difluorophenyl)thio]-N-1,2,4-thiadiazol-5-ylbenzenesulfonamide;

3-cyano-4-{[2-pyridazin-4-yl-4-(trifluoromethyl)phenyl]thio}-N-1,2,4-thiadiazol-5-ylbenzenesulfonamide;

5-chloro-2-fluoro-4-{[2-pyridazin-4-yl-4-(trifluoromethyl)phenyl]thio}-N-1,3,4-thiadiazol-2-ylbenzenesulfonamide;

4-{[2-(2-aminopyridin-4-yl)-4-(trifluoromethyl)phenyl]thio}-5-chloro-2-fluoro-N-1,3,4-thiadiazol-2-ylbenzenesulfonamide hydrochloride;

3-cyano-4-[2-methoxy-4-(trifluoromethyl)benzyl]-N-1,2,4-thiadiazol-5-ylbenzenesulfonamide;

3-cyano-4-[2-pyridazin-4-yl-4-(trifluoromethyl)benzyl]-N-1,2,4-thiadiazol-5-ylbenzenesulfonamide;

3-cyano-4-[(2-methoxy-4-(trifluoromethyl)phenyl)thio]-N-1,2,4-thiadiazol-5-ylbenzenesulfonamide; and 4-{[2-(2-aminopyridin-4-yl)-4-(trifluoromethyl)phenyl]thio}-5-chloro-2-fluoro-N-pyrimidin-2-ylbenzenesulfonamide;

or a pharmaceutically acceptable salt thereof.

Alkyl and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon atom. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, thiazolyl, isothiazolyl, thiadiazolyl, pyridyl, pyridazinyl, pyrimidinyl and pyrazinyl.

$Het^2$ may be attached via a ring nitrogen atom (when the heterocycle is attached to a carbon atom) or a ring carbon atom (in all cases). When substituted, and valency permitting, the substituent may be located on a ring nitrogen atom or a ring carbon atom. Specific examples of $Het^1$ include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO⁻Na⁺, —COO⁻K⁺, or —SO₃⁻Na⁺) or non-ionic (such as —N⁻N⁺(CH₃)₃) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994).

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino groups. The protecting groups used in the preparation of the compounds of the invention may be used in conventional manner. See, for example, those described in 'Greene's Protective Groups in Organic Synthesis' by Theodora W Greene and Peter G M Wuts, fourth edition, (John Wiley and Sons, 2006), in particular chapter 7 ("Protection for the Amino Group"), incorporated herein by reference, which also describes methods for the removal of such groups.

In the following general methods, X, $Y^1$, $Y^2$, Z, $R^1$, $R^2$, and $R^3$ are as previously defined for a compound of formula (I) unless otherwise stated. $R^{pg}$ is a suitable amino protecting group, such as dimethoxybenzyl, tert-butyloxycarbonyl, tert-butyl, methoxymethyl or ethoxyethyl. R is alkyl, such as $(C_1-C_6)$alkyl (e.g. methyl) or, when part of the moiety —$B(OR)_2$, may also be H or each R, together with the O atom to which it is attached, forms a cyclic boronic ester moiety, such as

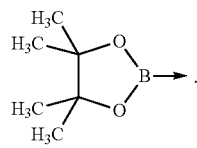

According to a first process, compounds of formula (I) wherein X is S may be prepared from compounds of formula (VI) by the process illustrated in Scheme 1.

Compounds of formula (I) can be prepared from compounds of formula (II) according to reaction step (v) by deprotection in the presence of an acid. Suitable acids include HCl, formic acid or trifluoroacetic acid. Preferred methods comprise trifluoroacetic acid in dichloromethane or neat trifluoroacetic acid at from room temperature to 55° C.

Alternatively, if the protecting group is dimethoxybenzyl, compounds of formula (I) can be prepared from compounds of formula (II) under basic conditions, such as sodium bicarbonate in ethanol/water at 80° C., or by heating in an appropriate solvent such as ethanol or toluene at temperatures exceeding 70° C.

In a further alternative, compounds of formula (I) can be prepared from compounds of formula (V) according to process step (iv) by nucleophilic aromatic substitution reaction with a thiophenol of formula (III) under basic reaction conditions. Suitable conditions include potassium carbonate in DMA or DMF, or sodium hydride in NMP or DMF. Preferred conditions comprise 2 equivalents of potassium carbonate in DMF at 90° C.

Compounds of formula (II) can be prepared from compounds of formula (IV) according to reaction step (iv) by nucleophilic aromatic substitution reaction with a thiophenol of formula (III) as described just above.

Compounds of formula (IV) can be prepared from compounds of formula (VI) and (VII) according to reaction step (iii) by displacement of a sulfonyl chloride with $HNR^{pg}Z$ under basic reaction conditions. Typical conditions comprise lithium hexamethyldisilazane in THF from −78° C. to ambient temperature.

Alternatively, compounds of formula (IV) can be prepared from compounds of formula (V) according to reaction step (ii) by introduction of a suitable amino protecting group $R^{pg}$. This can be effected under basic reaction conditions, such as di-tert-butyldicarbonate and triethylamine in THF; chloromethyl methyl ether and diisopropylethylamine in methylene Scheme 1

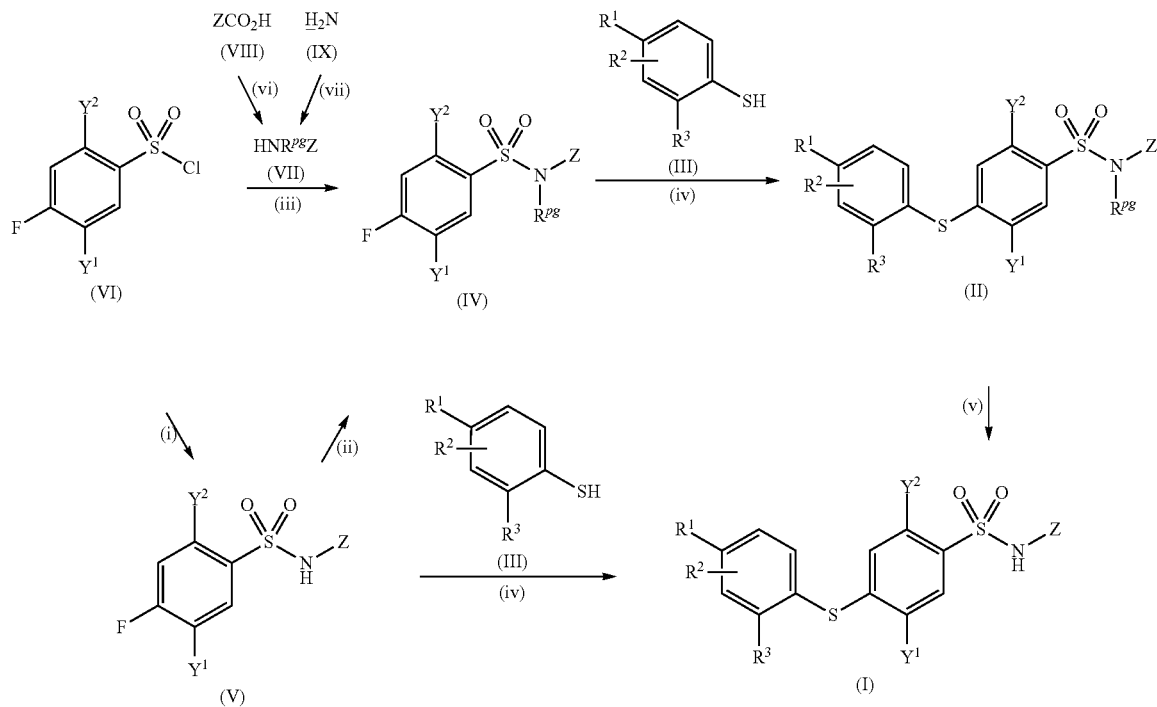

chloride; or chloromethyl ethyl ether and diisopropylethylamine in methylene chloride; or under Mitsunobu reaction conditions, such as dimethoxybenzylalcohol, diisopropylazodicarboxylate and triphenylphosphine in THF.

Compounds of formula (V) can be prepared from compounds of formula (VI) according to reaction step (i) by displacement of a sulfonyl chloride in the presence of a base, such as lithium hexamethyldisilazane, diazabicyclo(2.2.2)octane, triethylamine, NaOH or pyridine. Preferred conditions comprise NaOH in 1,4-dioxane or pyridine in dichloromethane at room temperature.

Compounds of formula (VII) can be prepared from compounds of formula (VIII) according to reaction step (vi) by Curtius rearrangement through generation of an acyl azide using diphenylphosphoryl azide. Preferred conditions comprise diphenylphosphoryl azide and triethylamine with tert-butanol in toluene at 90° C.

Alternatively compounds of formula (VII) may be prepared from compounds of formula (IX) according to reaction step (vii) by introduction of a suitable amino protecting group $R^{pg}$ through the processes outlined for reaction step (ii) or by reductive amination with an aldehyde. Typical reaction conditions comprise dimethoxybenzaldehyde in toluene at 110° C. followed by reduction with sodium borohydride.

According to another process, compounds of formula (I) where X is $CH_2$ may be prepared from compounds of formula (X) by the process illustrated in Scheme 2.

Compounds of formula (I) can be prepared from compounds of formula (II) according to reaction step (vi) by suitable deprotection methods as described above in Scheme 1, step (v).

Compounds of formula (II) can be prepared from compounds of formula (XIII) by process step (v), a cross-coupling reaction, with compounds of formula (XIV), in the presence of a suitable catalyst system, (e.g. palladium), and a base. Preferably the reaction is carried out under Suzuki reaction conditions. Preferred Suzuki conditions comprise 1.1 equivalents of boronic acid, 3 equivalent of $K_2CO_3$ and 0.1 equivalents $Pd(PPh_3)_4$ in THF/water at 65° C.

Compounds of formula (XIII) can be prepared from compounds of formula (XII) by process step (iii), a cross coupling reaction, with a boronic ester of formula (XV), such as bis(pinacolato)diboron or bis(neopentylgylcolato)diboron, in the presence of a suitable catalyst system (e.g. palladium) and base. Preferably the reaction is carried out under Suzuki reaction conditions. Preferred 'Suzuki' conditions comprise 1.05 equivalents of boronic ester, 3 equivalents of potassium acetate and 0.05 equivalents bis(diphenylphosphino)ferrocene palladium (II) chloride, dichloromethane complex in THF at 68° C.

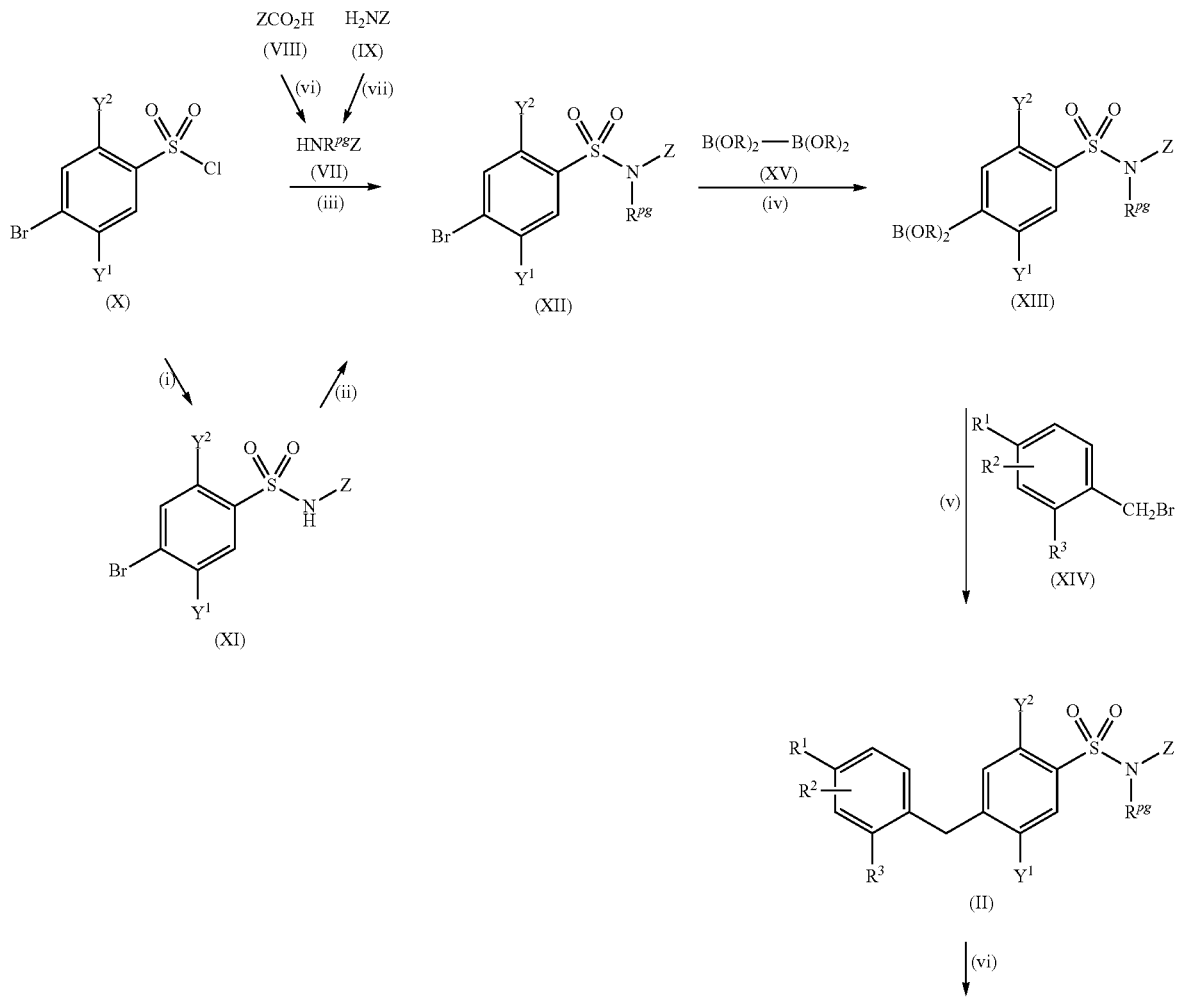

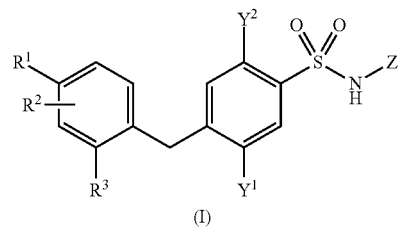

(I)

Compounds of formula (XII) can be prepared from compounds of formula (X) and (VII) according to reaction step (iii) under conditions described above in Scheme 1, step (iii).

Alternatively, compounds of formula (XII) can be prepared from compounds of formula (XI) according to reaction step (ii) under conditions described above in Scheme 1, step (ii).

Compounds of formula (XI) can be prepared from compounds of formula (X) according to reaction step (i) under conditions described above in Scheme 1, step (i).

Compounds of formula (VII) can be prepared from compounds of formula (VIII) according to reaction step (vi) or (vii) under, respectively, conditions described above in Scheme 1, step (vi) or (vii).

Compounds of formulae (III), (VI), (VIII), (IX), (X), (XIV) and (XV) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
an alternative Nav1.7 channel modulator, such as another compound of the present invention or a compound disclosed in WO 2009/012242;
an alternative sodium channel modulator, such as a Nav1.3 modulator (e.g. as disclosed in WO2008/118758); or a Nav1.8 modulator (e.g. as disclosed in WO 2008/

135826, more particularly N-[6-Amino-5-(2-chloro-5-methoxyphenyl)pyridin-2-yl]-1-methyl-1H-pyrazole-5-carboxamide);

an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;

a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene-1-carboxamide);

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H₁ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a 5-HT$_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,4,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-yrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyloctanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a microsomal prostaglandin E synthase type 1 (mPGES-1) inhibitor;

a leukotriene B4 antagonist, such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870; and a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid,
$Cs_2CO_3$ is caesium carbonate;
Cu(acac)$_2$ is copper (II) acetylacetonate;
CuI is copper (I) iodide;
Cu(OAc)$_2$ is copper (II) acetate;
DAD is diode array detector;
DCM is dichloromethane; methylene chloride;
DIPEA is N-ethyldiisopropylamine, N,N-diisopropylethylamine;
DMAP is 4-dimethylaminopyridine;
DMA is dimethylacetamide;

DMF is N,N-dimethylformamide;
DMSO is dimethyl sulphoxide;
EDTA is ethylenediaminetetraacetic acid;
ELSD is evaporative light scattering detection;
Et$_2$O is diethyl ether;
EtOAc is ethyl acetate;
EtOH is ethanol;
HCl is hydrochloric acid;
IPA is isopropanol;
Ir$_2$(OMe)$_2$COD$_2$ is bis(1,5-cyclooctadiene)di-μ-methoxy-diiridium (I);
K$_2$CO$_3$ is potassium carbonate;
KHSO$_4$ is potassium hydrogen sulphate;
KOAc is potassium acetate;
KOH is potassium hydroxide;
K$_3$PO$_4$ is potassium phosphate tribasic;
LCMS is liquid chromatography mass spectrometry (R$_t$=retention time);
LiOH is lithium hydroxide;
MeOH is methanol;
MgSO$_4$ is magnesium sulphate;
NaH is sodium hydride;
NaHCO$_3$ is sodium hydrogencarbonate;
Na$_2$CO$_3$ is sodium carbonate;
NaHSO$_3$ is sodium bisulphate;
NaHSO$_4$ is sodium hydrogensulphate;
NaOH is sodium hydroxide;
Na$_2$SO$_4$ is sodium sulphate;
NH$_4$Cl is ammonium chloride;
NMP is N-methlypyrollidone;
Pd/C is palladium on carbon;
Pd(PPh$_3$)$_4$ is palladium tetrakis;
Pd(dppf)$_2$Cl$_2$ is [1,1'-bis(diphenylphosphino)ferrocene] dichloropalladium(II), complex with dichloromethane;
THF is tetrahydrofuran;
THP is tetrahydropyran;
TLC is thin layer chromatography; and
WSCDI is 1-(3-dimethylaminopropyl)-3-ethylcarbodiimide hydrochloride.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol.

Mass spectra, MS (m/z), were recorded using either electrospray ionisation (ESI) or atmospheric pressure chemical ionisation (APCI). When relevant, and unless stated otherwise, the m/z data provided are for isotopes $^{19}$F, $^{35}$Cl and $^{79}$Br.

Automated Preparative High Performance Liquid Chromatography (HPLC)

Certain compounds of the Examples and Preparations were purified using Automated Preparative High Performance Liquid Chromatography (HPLC). Reversed-phase HPLC conditions were either on FractionLynx systems or on a Trilution system.

In the case of the Fractionlynx system, Samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 μm). B-HPLC was carried out on an Xterra Prep MS C18 (19×100 mm, 5 μm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 30 v Capillary: 3.20 kv
ES− Cone voltage: −30 v Capillary: −3.00 kv
Desolvation gas: 600 L/hr
Source Temp: 120° C.
Scan range 150-900 Da The fraction collection was triggered by both MS and ELSD.

Quality control (QC) analysis was performed using a LCMS method. Acidic runs were carried out on a Sunfire C18 (4.6×50 mm, 5 μm), basic runs were carried out on a Xterra C18 (4.6×50 mm, 5 μm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 25 v Capillary: 3.30 kv
ES− Cone voltage: −30 v Capillary: −2.50 kv
Desolvation gas: 800 L/hr
Source Temp: 150° C.
Scan range 160-900 Da Where the reversed-phase Trilution system was used (T-HPLC) the conditions were as follows:
Mobile phase A: 0.1% formic acid in water
Mobile phase B: 0.1% formic acid in acetonitrile
Column: Phenomenex C18 Luna 21.5 mm×15 cm with 5 micron particule size
Gradient: 95-5% A over 15 min, 15 min hold, 15 ml/min flow rate
UV: 200 nm-400 nm
Temperature: Room temperature
Liquid Chromatography Mass Spectrometry Unless carried out by Auto-HPLC (under conditions of A-HPLC or B-HPLC) as just described, LCMS conditions were run according to one of the conditions given below (where ratios of solvents are given, the ratios are by volume):
Acidic 2 minute LCMS
Mobile phase A: 0.1% formic acid in water
Mobile phase B: 0.1% formic acid in 70% methanol: 30% isopropanol
Column: C18 phase Phenomenex 20×4.0 mm with 3 micron particle size
Gradient: 98-10% A over 1.5 min, 0.3 min hold, 0.2 re-equilbration, 2 ml/min flow rate
UV: 210 nm-450 nm DAD
Temperature: 75° C.
Or
Mobile phase A: 0.1% formic acid in water
Mobile phase B: 0.1% formic acid in acetonitrile Column: C18 phase Phenomenex 20×4.0 mm with 3 micron particle size Gradient: 70-2% A over 1.5 min, 0.3 min hold, 0.2 re-equilbration, 1.8 ml/min flow rate UV: 210 nm-450 nm DAD Temperature: 75° C.

Acidic 4.5 Minute LCMS

Mobile phase A: 0.05% formic acid in water

Mobile phase B: acetonitrile

Column: Phenomenex Gemini C18 45×45 mm with 5 micron particle size

Gradient: 80-50% A over 0.5 min, 50-2% A over 3 min, 1 min hold, 0.2 min re-equilibration, 2.0 ml/min flow rate UV: 220 nm-254 nm DAD Temperature: 40° C.

Acidic 8 Minute LCMS

Mobile phase A: 0.05% formic acid in water

Mobile phase B: acetonitrile

Column: Phenomenex Gemini C18 45×45 mm with 5 micron particle size

Gradient: 80-50% A over 0.5 min, 50-2% A over 3 min, 4.5 min hold, 0.2 min re-equilibration, 2.0 ml/min flow rate UV: 220 nm-254 nm DAD Temperature: 40° C.

Acidic 6 Minute LCMS

Mobile phase A: 0.1% formic acid in water

Mobile phase B: 0.1% formic acid in acetonitrile

Column: C18 phase Waters Sunfire 50×4.6 mm with 5 micron particle size

Gradient: 95-5% A over 3 min, 1 min hold, 2 min re-equilibration, 1.5 ml/min flow rate UV: 210 nm-450 nm DAD Temperature: 50° C.

Basic 6 Minute LCMS

Mobile phase A: 0.1% ammonium hydroxide in water

Mobile phase B: 0.1% ammonium hydroxide in acetonitrile

Column: C18 phase Fortis 50×4.6 mm with 5 micron particle size

Gradient: 95-5% A over 3 min, 1 min hold, 2 min re-equilibration, 1 ml/min flow rate UV: 210 nm-450 nm DAD Temperature: 50° C.

Acidic 30 Minute LCMS

Mobile phase A: 0.1% formic acid in water

Mobile phase B: 0.1% formic acid in acetonitrile

Column: Phenomenex C18 phase Gemini 150×4.6 mm with 5 micron particle size

Gradient: 98-2% A over 18 min, 2 min hold, 1 ml/min flow rate

UV: 210 nm-450 nm DAD

Temperature: 50° C.

Basic 30 Minute LCMS

Mobile phase A: 10 mM ammonium acetate in water

Mobile phase B: 10 mM ammonium acetate in methanol

Column: Phenomenex Phenyl Hexyl 150×4.6 mm with 5 micron particle size

Gradient: 98-2% A over 18 min, 2 min hold, 1 ml/min flow rate

UV: 210 nm-450 nm DAD

Temperature: 50° C.

In the tabulated experimental details that follow, the Examples and Preparations were prepared according to the corresponding reference method (i.e. PROCESS A, PROCESS B, Preparation 28, and so on). The skilled person will appreciate that, in the synthesis of any specific Example or Preparation, it may be desirable to make minor variations to the reaction conditions of the reference method (e.g. with regard to solvent, temperature and so on).

PROCESS A

Process According to Scheme 1, Step (v)

EXAMPLE 1

5-Chloro-2-fluoro-N-1,3,4-thiadiazol-2-yl-4-{[3-(trifluoromethyl)phenyl]thio}benzenesulfonamide

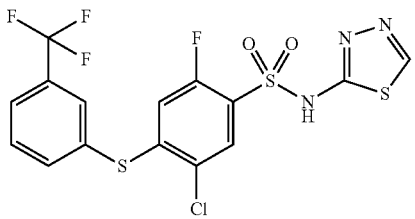 [SMILES: O=S(=O)(Nc1nncs1)c1cc(Cl)c(Sc2cccc(C(F)(F)F)c2)cc1F]

To 5-chloro-N-(2,4-dimethoxybenzyl)-2-fluoro-N-1,3,4-thiadiazol-2-yl-4-{[3-(trifluoromethyl)phenyl]thio}benzenesulfonamide (Preparation 3, 0.215 g, 0.347 mmol) was added a 4M solution of hydrogen chloride in 1,4-dioxane (5.04 mL). The reaction was stirred at ambient temperature for 5 hours before concentrating in vacuo. The residue was solubilised in dimethylsulfoxide (1 mL) and purified by the B-HPLC method to afford the title compound.

LCMS Rt=3.84 min MS m/z 469.9 [MH]+

PROCESS B

Process According to Scheme 1, Step (v)

EXAMPLE 2

5-Chloro-2-fluoro-4-[(4-methoxyphenyl)thio]-N-1,3,4-thiadiazol-2-ylbenzenesulfonamide

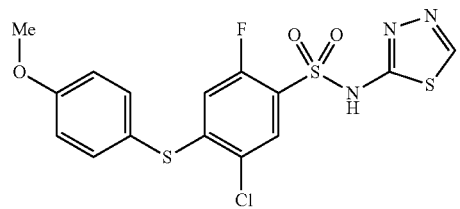 [SMILES: COc1ccc(Sc2cc(F)c(S(=O)(=O)Nc3nncs3)cc2Cl)cc1]

To 5-chloro-N-(2,4-dimethoxybenzyl)-2-fluoro-4-[(4-methoxyphenyl)thio]-N-1,3,4-thiadiazol-2-ylbenzenesulfonamide (Preparation 4, 0.224 g, 0.387 mmol) in 1,4-dioxane (1 mL) was added a 4M solution of hydrogen chloride in 1,4-dioxane (3 mL). The reaction was stirred under a nitrogen atmosphere at ambient temperature overnight before concentrating in vacuo. The residue was purified by silica gel flash chromatography to afford a white solid. The solid was further purified by reverse phase column chromatography (Trilution system) to afford the title compound as a solid (0.115 g, 69%).

$^1$HNMR (d$_6$-DMSO): δ 3.80 (s, 3H), 6.38 (m, 1H), 7.10 (m, 2H), 6.57 (m, 2H), 7.80 (m, 1H), 8.80 (s, 1H).

LCMS Rt=3.65 min MS m/z 431.78/433.73 [MH]+

PROCESS C

Process According to Scheme 1, Step (v)

EXAMPLE 3

3-Cyano-4-[(3-methoxyphenyl)thio]-N-1,2,4-thiadiazol-5-ylbenzenesulfonamide

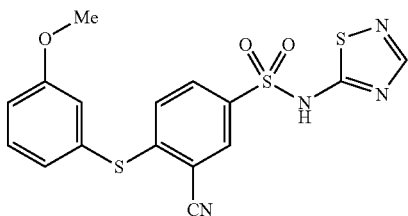 [SMILES: COc1cccc(Sc2ccc(S(=O)(=O)Nc3ncns3)cc2C#N)c1]

To 3-cyano-N-(2,4-dimethoxybenzyl)-4-[(3-methoxyphenyl)thio]-N-1,2,4-thiadiazol-5-ylbenzenesulfonamide (Preparation 17, 0.204 g, 0.368 mmol) was added a 4M solution of hydrogen chloride in 1,4-dioxane. The reaction was stirred at ambient temperature overnight. The reaction was quenched with methanol and passed through a plug of Arbocel™ to give a pale yellow solution. The solution was concentrated in vacuo to give a yellow solid. The solid was purified by silica gel flash column chromatography to give a white solid (0.141 g, 95%).

$^1$HNMR (CD$_3$OD): δ 3.79 (s, 3H), 7.00-7.10 (m, 4H), 7.34-7.43 (m, 1H), 7.85-7.97 (m, 2H), 8.12 (s, 1H).

LCMS Rt=6.80 min MS m/z 404.9 [MH]+, 402.8 [MH]−

The following examples were prepared by Processes A or B, from the appropriate 2,4-dimethoxybenzyl precursor of formula (II).

| Ex | Name | Data | Process |
|---|---|---|---|
| 4 | 5-chloro-2-fluoro-4-[(3-methoxyphenyl)thio]-N-1,3,4-thiadiazol-2-ylbenzenesulfonamide | LCMS Rt = 2.31 min (basic QC method) MS m/z 431.9 [MH]+ | A |
| 5 | 5-chloro-2-fluoro-N-1,3,4-thiadiazol-2-yl-4-{[2-(trifluoromethyl)phenyl]thio}benzenesulfonamide | LCMS Rt = 3.74 min MS m/z 469.80/471.72 [MH]+ | B |
| 6 | 5-chloro-2-fluoro-4-[(3-fluorophenyl)thio]-N-1,3,4-thiadiazol-2-ylbenzenesulfonamide | LCMS Rt = 3.66 min (acidic QC method) MS m/z 419.9 [MH]+ | A |
| 7 | 5-chloro-2-fluoro-4-[(2-fluorophenyl)thio]-N-1,3,4-thiadiazol-2-ylbenzenesulfonamide | LCMS Rt = 3.58 min (acidic QC method) MS m/z 419.9 [MH]+ | A |
| 8 | 5-chloro-2-fluoro-4-[(2-methoxyphenyl)thio]-N-1,3,4-thiadiazol-2-ylbenzenesulfonamide | LCMS Rt = 3.57 min (acidic QC method) MS m/z 431.9 [MH]+ | A |
| 9 | 5-chloro-4-[(3,4-difluorophenyl)thio]-2-fluoro-N-1,3,4-thiadiazol-2-ylbenzenesulfonamide | LCMS Rt = 3.54 min MS m/z 437.78/439.80 [MH]+ | B |
| 10 | 5-chloro-2-fluoro-N-1,3,4-thiadiazol-2-yl-4-{[4-(trifluoromethyl)phenyl]thio}benzenesulfonamide | LCMS Rt = 2.59 min (basic QC method) MS m/z 469.9 [MH]+ | A |

The following examples were prepared by Processes A or C, from the appropriate 2,4-dimethoxybenzyl precursor of formula (II).

| Ex | Name | Data | Process |
|---|---|---|---|
| 11 | 3-cyano-4-[(4-methoxyphenyl)thio]-N-1,2,4-thiadiazol-5-ylbenzenesulfonamide | LCMS Rt = 2.24 min MS m/z 405 [MH]+ | A |
| 12 | 3-cyano-4-[(2-methoxyphenyl)thio]-N-1,2,4-thiadiazol-5-ylbenzenesulfonamide | LCMS Rt = 6.43 min MS m/z 404.8 [MH]+, 402.8 [MH]− | C |
| 13 | 3-cyano-N-1,2,4-thiadiazol-5-yl-4-{[3-(trifluoromethyl)phenyl]thio}benzenesulfonamide | LCMS Rt = 7.22 min MS m/z 442.8 [MH]+, 440.8 [MH]− | C |
| 14 | 3-cyano-N-1,2,4-thiadiazol-5-yl-4-{[4-(trifluoromethyl)phenyl]thio}benzenesulfonamide | LCMS Rt = 4.04 min MS m/z 443.2 [MH]+, 441.2 [MH]− | C |

EXAMPLE 15

3-Cyano-4-[(2-fluorophenyl)thio]-N-1,2,4-thiadiazol-5-ylbenzenesulfonamide

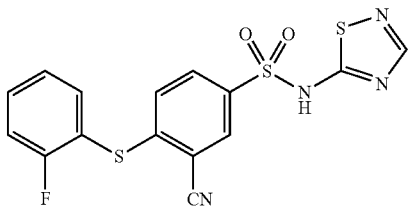 [SMILES: N#Cc1cc(S(=O)(=O)Nc2ncns2)ccc1Sc1ccccc1F]

To 3-cyano-N-(2,4-dimethoxybenzyl)-4-[(2-fluorophenyl)thio]-N-1,2,4-thiadiazol-5-ylbenzenesulfonamide (Preparation 13, 0.320 g, 0.590 mmol) was added a 4M solution of hydrogen chloride in 1,4-dioxane (10 mL). The reaction was stirred at ambient temperature overnight before concentrating in vacuo. The residue purified by silica gel flash column chromatography (ethyl acetate:methanol elution) followed by reverse phase column chromatography to afford the title compound as a solid (0.055 g, 24%).

$^1$HNMR ($d_6$-acetone): δ 7.18 (m, 1H), 7.4 (m, 2H), 7.7 (m, 2H), 8.0 (m, 1H), 8.2 (s, 1H), 8.4 (s, 1H).

EXAMPLE 16

3-Cyano-N-1,2,4-thiadiazol-5-yl-4-{[2-(trifluoromethyl)phenyl]thio}benzenesulfonamide

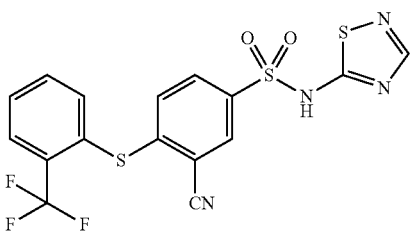 [SMILES: N#Cc1cc(S(=O)(=O)Nc2ncns2)ccc1Sc1ccccc1C(F)(F)F]

2-Trifluoromethylthiophenol (0.0615 g, 0.345 mmol) and potassium carbonate (0.100 g, 0.724 mmol) were stirred in N,N-dimethylacetamide (3 mL). After 5 minutes, 3-cyano-N-(2,4-dimethoxybenzyl)-4-fluoro-N-1,2,4-thiadiazol-5-ylbenzenesulfonamide (Preparation 1, 0.150 g, 0.345 mmol) was added to the reaction mixture and the mixture stirred at ambient temperature overnight. The mixture was partitioned between ethyl acetate and water. The organic layer was washed with a 1M aqueous solution of sodium hydroxide, followed by brine, then dried over MgSO$_4$, filtered and concentrated in vacuo to give a residue. The residue was then dissolved in 1,4-dioxane (1 mL) and a 4M solution of hydrogen chloride in 1,4-dioxane added. The reaction mixture was stirred at ambient temperature overnight. The reaction mixture was concentrated in vacuo to give a residue. The residue was solubilised in dimethylsulfoxide (1 mL) and purified by the B-HPLC method to afford the title compound.

LCMS Rt=2.37 min (basic QC method) MS m/z 442.98 [MH]+

EXAMPLE 17

3-Cyano-4-[(3,4-difluorophenyl)thio]-N-1,2,4-thiadiazol-5-ylbenzenesulfonamide

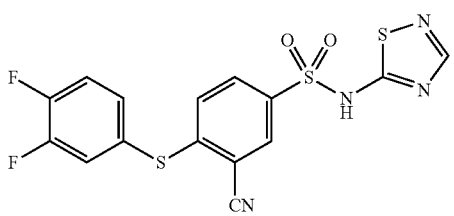 [SMILES: N#Cc1cc(S(=O)(=O)Nc2ncns2)ccc1Sc1ccc(F)c(F)c1]

3,4-Difluorothiophenol (0.101 g, 0.690 mmol) and potassium carbonate (0.200 g, 1.45 mmol) were stirred in N,N-dimethylacetamide (3 mL). After 5 minutes, 3-cyano-N-(2,4-dimethoxybenzyl)-4-fluoro-N-1,2,4-thiadiazol-5-ylbenzenesulfonamide (Preparation 1, 0.300 g, 0.690 mmol) was added to the reaction mixture and the mixture stirred at ambient temperature overnight. The mixture was partitioned between ethyl acetate and water. The organic layer was washed with a 1M aqueous solution of sodium hydroxide, followed by brine, then dried over MgSO$_4$, filtered and concentrated in vacuo to give a white solid. The solid was then dissolved in 1,4-dioxane and a 4M solution of hydrogen chloride in 1,4-dioxane (3 mL) added. The reaction mixture was stirred at ambient temperature overnight. The reaction mixture was concentrated in vacuo to give a residue. The residue was solubilised in dimethylsulfoxide (1 mL) and purified by the B-HPLC method to afford the title compound.

LCMS Rt=4.23 min (acidic QC method) MS m/z 411 [MH]+

EXAMPLE 18

3-Cyano-4-{[2-pyridazin-4-yl-4-(trifluoromethyl)phenyl]thio}-N-1,2,4-thiadiazol-5-ylbenzenesulfonamide

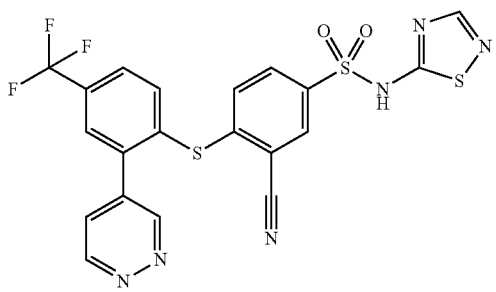 [SMILES: N#Cc1cc(S(=O)(=O)Nc2ncns2)ccc1Sc1ccc(C(F)(F)F)cc1-c1ccnnc1]

Prepared according to Method A using 3-cyano-N-(2,4-dimethoxybenzyl)-4-{[2-pyridazin-4-yl-4-(trifluoromethyl)phenyl]thio}-N-1,2,4-thiadiazol-5-ylbenzenesulfonamide (Preparation 22, 95 mg, 0.142 mmol). The title compound was purified by the B-HPLC method LCMS Rt=3.82 min (acidic QC method) MS m/z 521.0 [MH]+

EXAMPLE 19

5-Chloro-2-fluoro-4-{[2-pyridazin-4-yl-4-(trifluoromethyl)phenyl]thio}-N-1,3,4-thiadiazol-2-ylbenzenesulfonamide

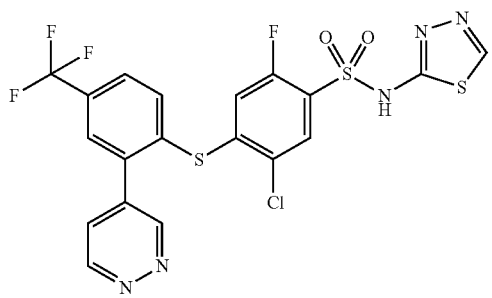 [SMILES: O=S(=O)(Nc1nncs1)c1cc(Cl)c(Sc2ccc(C(F)(F)F)cc2-c2ccnnc2)cc1F]

Prepared according to Method A using 5-chloro-N-(2,4-dimethoxybenzyl)-2-fluoro-4-{[2-pyridazin-4-yl-4-(trifluoromethyl)phenyl]thio}-N-1,3,4-thiadiazol-2-ylbenzenesulfonamide (Preparation 23, 95 mg, 0.136 mmol). The title compound was purified by the B-HPLC method.

LCMS Rt=2.62 min (basic QC method) MS m/z 548.0 [MH]+

EXAMPLE 20

4-{[2-(2-Aminopyridin-4-yl)-4-(trifluoromethyl)phenyl]thio}-5-chloro-2-fluoro-N-1,3,4-thiadiazol-2-ylbenzenesulfonamide hydrochloride

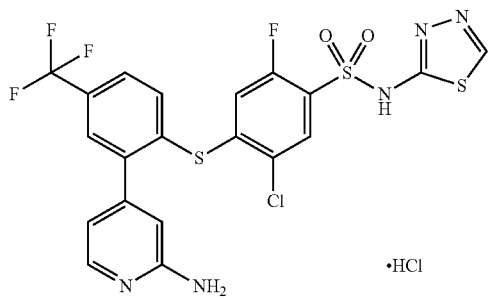 [SMILES: Nc1cc(-c2cc(C(F)(F)F)ccc2Sc2cc(F)c(S(=O)(=O)Nc3nncs3)cc2Cl)ccn1 ; Cl]

4-{[2-(2-Aminopyridin-4-yl)-4-(trifluoromethyl)phenyl]thio}-5-chloro-N-(2,4-dimethoxybenzyl)-2-fluoro-N-1,3,4-thiadiazol-2-ylbenzenesulfonamide (Preparation 26, 0.153 g, 74.4 mmol) was dissolved in dichloromethane (3 mL). Trifluoroacetic acid (3 mL) was added and the mixture stirred at room temperature under nitrogen for 3 hours. Solvents were removed in vacuo and the residue diluted in ethyl acetate (10 mL) before washing with an aqueous solution of hydrochloric acid (10 mL, 2.0 M). The organic layer was collected, dried over sodium sulphate, filtered and concentrated in vacuo. The title compound was purified by trituration in a mixture of tert-butylmethylether and dichloromethane (2:1) to give the title compound as a white solid (0.021 g, 15%).

$^1$HNMR (d$_6$-DMSO): δ 6.88 (dd, 1H), 6.91 (m, 1H), 7.10 (d, 1H), 7.75 (dd, 1H), 7.82 (dd, 1H), 7.88 (m, 2H), 7.96 (d, 1H), 7.71-7.91 (br s, 2H), 8.82 (s, 1H).

LCMS Rt=1.05 min MS m/z 561.9 [MH]+

EXAMPLE 21

3-Cyano-4-[2-methoxy-4-(trifluoromethyl)benzyl]-N-1,2,4-thiadiazol-5-ylbenzenesulfonamide

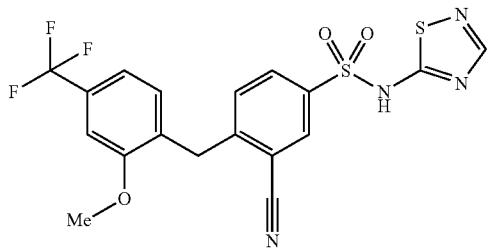 [SMILES: COc1cc(C(F)(F)F)ccc1Cc1ccc(S(=O)(=O)Nc2ncns2)cc1C#N]

3-Cyano-N-(2,4-dimethoxybenzyl)-4-[2-methoxy-4-(trifluoromethyl)benzyl]-N-1,2,4-thiadiazol-5-ylbenzenesulfonamide (Preparation 30, 33.8 mg, 0.056 mmol) was dissolved in dichloromethane (1 mL) and cooled to 0° C. Trifluoroacetic acid (22 µL, 0.28 mmol) was added and the reaction stirred for 3 hours warming slowly to room temperature. The solvent was removed in vacuo and the residue re-dissolved in methanol (~5 mL). Once again the solvent was removed in vacuo. The material was suspended in methanol (5 mL) and filtered through Celite™. The reaction mixture was concentrated in vacuo and purified by the B-HPLC method to afford the title compound.

LCMS Rt=4.07 min (acidic QC method) MS m/z 453 [MH]−, 455 [MH+]

EXAMPLE 22

3-Cyano-4-[2-pyridazin-4-yl-4-(trifluoromethyl)benzyl]-N-1,2,4-thiadiazol-5-ylbenzenesulfonamide

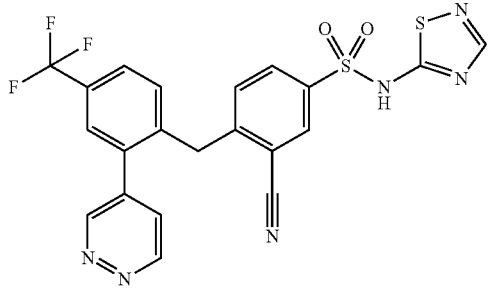 [SMILES: N#Cc1cc(S(=O)(=O)Nc2ncns2)ccc1Cc1ccc(C(F)(F)F)cc1-c1ccnnc1]

3-Cyano-N-(2,4-dimethoxybenzyl)-4-[2-pyridazin-4-yl-4-(trifluoromethyl)benzyl]-N-1,2,4-thiadiazol-5-ylbenzenesulfonamide (Preparation 34, 54 mg, 0.083 mmol) was dissolved in dichloromethane (0.75 mL) and cooled to 0° C. Trifluoroacetic acid (32 µL, 0.41 mmol) was added as a solution in dichloromethane (0.25 mL) and the reaction stirred for 2 hours warming slowly to room temperature. The solvent was removed in vacuo and the residue re-dissolved in methanol. Once again the solvent was removed in vacuo. The material was suspended in methanol and filtered through Celite™. The reaction mixture was concentrated in vacuo and purified by the basic preparative HPLC method to afford the title compound.

LCMS Rt=2.31 min (basic QC method) MS m/z 501 [MH]−, 503 [MH+]

EXAMPLE 23

3-Cyano-4-[(2-methoxy-4-(trifluoromethyl)phenyl)thio]-N-1,2,4-thiadiazol-5-ylbenzenesulfonamide

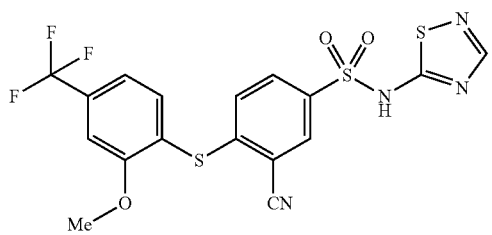 [SMILES: COc1cc(C(F)(F)F)ccc1Sc1ccc(S(=O)(=O)Nc2ncns2)cc1C#N]

Prepared according to Method B using 3-Cyano-N-(2,4-domethoxybenzyl)-4-[(2-methoxy-4-(trifluoromethyl)phenyl)thio]-N-1,2,4-thiadiazol-5-ylbenzenesulfonamide (Preparation 35, 48 mg, 0.077 mmol). Purified using silica gel column chromatography (10% methanol in ethyl acetate) to afford the title compound as a colourless oil (27 mg, 77%).

$^1$HNMR (CD$_3$OD): δ 3.82 (s, 3H), 7.18 (m, 1H), 7.26-7.32 (m, 2H), 7.50 (m, 1H), 7.93 (m, 2H), 8.17 (s, 1H).

LCMS Rt=7.74 min MS m/z 471 [MH]+

EXAMPLE 24

4-{[2-(2-Aminopyridin-4-yl)-4-(trifluoromethyl)phenyl]thio}-5-chloro-2-fluoro-N-pyrimidin-2-yl-benzenesulfonamide

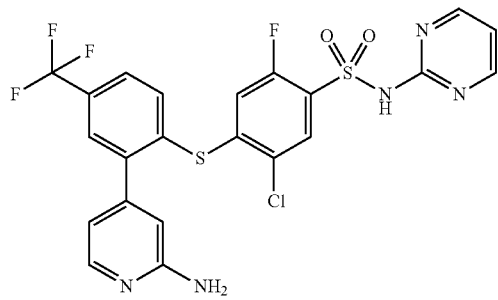 [SMILES: Nc1cc(-c2cc(C(F)(F)F)ccc2Sc2cc(F)c(S(=O)(=O)Nc3ncccn3)cc2Cl)ccn1]

Prepared according to Method B using 4-{[2-(2-Aminopyridin-4-yl)-4-(trifluoromethyl)phenyl]thio}-5-chloro-2-fluoro-N-(2,4-dimethoxybenzyl)-pyrimidin-2-ylbenzenesulfonamide (Preparation 36, 298 mg, 0.42 mmol). Purified using silica gel column chromatography (2%-15% methanol in dichloromethane gradient elution) followed by a second silica gel column chromatography (0%-10% methanol in ethyl acetate gradient elution) to afford the title compound (60 mg, 25%).

$^1$HNMR (d$_6$-DMSO): δ 6.22 (br s, 2H), 6.41 (s, 1H), 6.48 (m, 1H), 6.95-7.02 (m, 2H), 7.55 (m, 1H), 7.67 (s, 1H), 7.78 (m, 1H), 7.88 (m, 1H), 7.92 (m, 1H), 8.45 (m, 2H).

LCMS Rt=1.51 min MS m/z 556 [MH]+

Preparation 1

3-Cyano-N-(2,4-dimethoxybenzyl)-4-fluoro-N-1,2,4-thiadiazol-5-ylbenzenesulfonamide

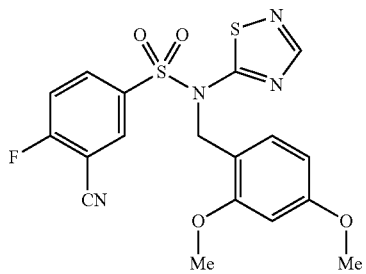 [SMILES: COc1ccc(CN(c2ncns2)S(=O)(=O)c2ccc(F)c(C#N)c2)c(OC)c1]

N-(2,4-Dimethoxybenzyl)-1,2,4-thiadiazol-5-amine (Preparation 18, 42.8 g, 170 mmol) was dissolved in anhydrous THF (600 mL) and stirred under a nitrogen atmosphere at −78° C. A 1M solution of LiHMDS in THF (238 mL, 238 mmol) was added dropwise over 30 minutes maintaining the temperature between −65° C. and −70° C. The reaction mixture was left at −78° C. for 5 minutes, then allowed to warm to −10° C. over 1.5 hours. Upon reaching −10° C., the brown reaction mixture was cooled to −78° C. again, and a solution of 3-cyano-4-fluorobenzene sulfonyl chloride (48.6 g, 221 mmol) in THF (200 mL) was added dropwise over 30 minutes maintaining the temperature between −65° C. and −70° C. The brown solution was allowed to warm gradually to ambient temperature and stirred overnight. The reaction mixture was diluted with ethyl acetate, washed with a saturated ammonium chloride solution, and extracting with further ethyl acetate. The combined organics were dried over MgSO$_4$, filtered and concentrated in vacuo to afford a brown residue. The residue was purified by silica gel column chromatography (10%-30% ethyl acetate in heptane gradient elution) to afford the title compound as a white solid (52.3 g, 71%).

$^1$HNMR (CDCl$_3$): δ 3.60 (s, 3H), 3.79 (s, 3H), 5.32 (s, 2H), 6.22 (s, 1H), 6.32-6.48 (m, 1H), 7.05-7.09 (m, 1H), 7.18-7.24 (m, 1H), 7.70-7.73 (m, 1H), 7.92-7.99 (m, 1H), 8.22 (s, 1H).

Preparation 2

5-Chloro-N-(2,4-dimethoxybenzyl)-2,4-difluoro-N-1,3,4-thiadiazol-2-ylbenzenesulfonamide

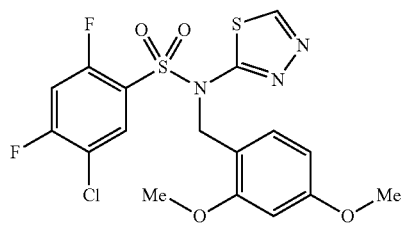 [SMILES: COc1ccc(CN(c2nncs2)S(=O)(=O)c2cc(Cl)c(F)cc2F)c(OC)c1]

N-(2,4-Dimethoxybenzyl)-1,3,4-thiadiazol-2-amine (Preparation 19, 203.4 g, 0.809 mol) was dissolved in 2-methyltetrahydrofuran (1.63 L) and the yellow suspension cooled to between −38° C. and −45° C. Lithium bis(trimethylsilyl)amide (890 mL of 1M solution in tetrahydrofuran, 0.890 mol) was added slowly over 15 minutes keeping the temperature between −38° C. and −45° C. to give an orange suspension. This orange suspension was stirred at −38° C. to −45° C. for 45 minutes and then a solution of 5-chloro-2,4-difluorobenzenesulfonyl chloride, (200 g, 0.809 mol) in 2-methyltetrahydrofuran (407 mL) added slowly over 20 minutes keeping the temperature between −38° C. and −45° C. The mixture was warmed to 15° C. over 1 hour. The reaction was quenched with a solution of ammonium chloride (203.4 g, 3.80 mol) in water (1.02 L) and stirred vigorously for 5 minutes. The layers were separated and the organic layer washed with water (813.6 mL) and concentrated in vacuo to give an orange solid which was triturated with isopropyl acetate (1.22 L) to afford the title compound as a yellow-orange solid (218.6 g, 58%).

$^1$HNMR (CDCl$_3$): δ 3.71 (s, 3H), 3.78 (s, 3H), 5.35 (m, 2H), 6.26 (m, 1H), 6.38 (m, 1H), 6.99 (m, 1H), 7.27 (m, 1H), 7.83 (m, 1H), 8.87 (m, 1H).

LCMS Rt=1.76 min MS m/z 484 [MNa]+

PROCESS D

Process According to Scheme 1, Step (iv)

Preparation 3

5-Chloro-N-(2,4-dimethoxybenzyl)-2-fluoro-N-1,3,4-thiadiazol-2-yl-4-{[3-(trifluoromethyl)phenyl]thio}benzenesulfonamide

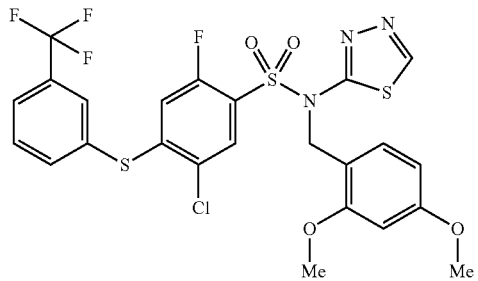 [SMILES: COc1ccc(CN(c2nncs2)S(=O)(=O)c2cc(Cl)c(Sc3cccc(C(F)(F)F)c3)cc2F)c(OC)c1]

To 3-(trifluoromethyl)thiophenol (0.116 g, 0.649 mmol) in dimethylsulfoxide (5 mL) was added potassium carbonate (0.254 g, 1.62 mmol) followed by 5-chloro-N-(2,4-dimethoxybenzyl)-2,4-difluoro-N-1,3,4-thiadiazol-2-ylbenzenesulfonamide (Preparation 2, 0.250 g, 0.541 mmol). The reaction mixture was stirred at ambient temperature overnight. The mixture was partitioned between dichloromethane and water and the layers separated by phase separation cartridge. The organic layer was concentrated in vacuo and the resulting residue purified by silica gel flash column chromatography (10%-20% ethyl acetate in heptane gradient elution) to afford the title compound as a solid (0.215 g, 64%).

$^1$HNMR (d$_6$-DMSO): δ 3.60 (s, 3H), 3.70 (s, 3H), 5.10 (s, 2H), 6.40 (m, 2H), 6.60 (m, 1H), 7.05 (m, 1H), 7.80 (m, 2H), 7.90-8.00 (m, 3H), 9.30 (m, 1H).

LCMS Rt=4.01 min MS m/z no mass ion observed

PROCESS E

Process According to Scheme 1, Step (iv)

Preparation 4

5-Chloro-N-(2,4-dimethoxybenzyl)-2-fluoro-4-[(4-methoxyphenyl)thio]-N-1,3,4-thiadiazol-2-ylbenzenesulfonamide

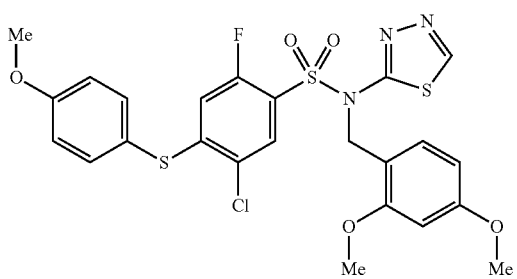 [SMILES: COc1ccc(Sc2cc(F)c(S(=O)(=O)N(Cc3ccc(OC)cc3OC)c3nncs3)cc2Cl)cc1]

5-Chloro-N-(2,4-dimethoxybenzyl)-2,4-difluoro-N-1,3,4-thiadiazol-2-ylbenzenesulfonamide (Preparation 2, 0.200 g, 0.433 mmol) and potassium carbonate (0.180 g, 1.30 mmol) were stirred in N,N-dimethylacetamide (1 mL). A solution of 4-methoxythiophenol (0.0576 g, 0.411 mmol) in N,N-dimethylacetamide (2 mL) was added dropwise to the reaction mixture and stirred at ambient temperature for 1 hour. The reaction was quenched with a 1M aqueous solution of sodium hydroxide whereupon a precipitate formed. The precipitate was collect by filtration to afford the title compound (0.224 g, 89%) and this was used in the next step without purification.

$^1$HNMR (d$_6$-DMSO): δ 3.60 (s, 3H), 3.70 (s, 3H), 3.80 (s, 3H), 5.08 (s, 2H), 6.28 (m, 1H), 6.40 (m, 2H), 7.05 (m, 1H), 7.15 (m, 2H), 7.55 (m, 2H), 7.70 (m, 1H), 9.27 (s, 1H)

LCMS Rt=4.62 min

The following Preparations were carried out according to Processes D or E, employing the appropriate thiol of formula (III) and 2,4-dimethoxybenzyl derivative of formula (IV).

| Pr | Name | Data | Method |
|---|---|---|---|
| 5 | 5-chloro-N-(2,4-dimethoxybenzyl)-2-fluoro-4-[(3-methoxyphenyl)thio]-N-1,3,4-thiadiazol-2-ylbenzenesulfonamide | LCMS Rt = 3.92 min MS m/z 604 [MNa]+ | D |
| 6 | 5-chloro-N-(2,4-dimethoxybenzyl)-2-fluoro-N-1,3,4-thiadiazol-2-yl-4-{[2-(trifluoromethyl)phenyl]thio}benzenesulfonamide | LCMS Rt = 4.60 min MS m/z 619.96 [MH]+ | E |
| 7 | 5-chloro-N-(2,4-dimethoxybenzyl)-2-fluoro-4-[(3-fluorophenyl)thio]-N-1,3,4-thiadiazol-2-ylbenzenesulfonamide | LCMS Rt = 3.66 min MS m/z 570 [MH]+ | D |
| 8 | 5-chloro-N-(2,4-dimethoxybenzyl)-2-fluoro-4-[(2-fluorophenyl)thio]-N-1,3,4-thiadiazol-2-ylbenzenesulfonamide | LCMS Rt = 4.30 min MS m/z 570 [MH]+ | D |

| Pr | Name | Data | Method |
|---|---|---|---|
| 9 | 5-chloro-N-(2,4-dimethoxybenzyl)-2-fluoro-4-[(2-methoxyphenyl)thio]-N-1,3,4-thiadiazol-2-ylbenzenesulfonamide | LCMS Rt = 4.30 min MS m/z 582 [MH]+ | D |
| 10 | 5-chloro-4-[(3,4-difluorophenyl)thio]-N-(2,4-dimethoxybenzyl)-2-fluoro-N-1,3,4-thiadiazol-2-ylbenzenesulfonamide | LCMS Rt = 4.33 min MS m/z no mass ion observed | E |
| 11 | 5-chloro-N-(2,4-dimethoxybenzyl)-2-fluoro-N-1,3,4-thiadiazol-2-yl-4-{[4-(trifluoromethyl)phenyl]thio}benzenesulfonamide | LCMS Rt = 4.00 min MS m/z 620 [MH]+ | D |

PROCESS F

Process According to Scheme 1, Step (iv)

Preparation 12

3-Cyano-N-(2,4-dimethoxybenzyl)-4-[(2-methoxyphenyl)thio]-N-1,2,4-thiadiazol-5-ylbenzenesulfonamide

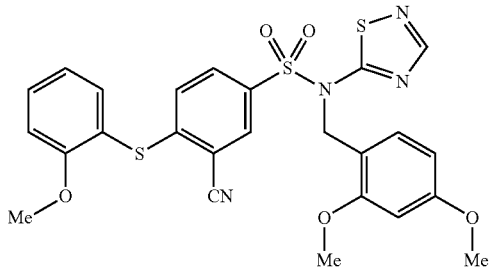 [SMILES: COc1ccc(CN(c2ncns2)S(=O)(=O)c2ccc(Sc3ccccc3OC)c(C#N)c2)c(OC)c1]

2-Methoxythiophenol (0.0322 g, 0.230 mmol) and potassium carbonate (0.158 g, 1.14 mmol) were stirred in N,N-dimethylacetamide. 3-Cyano-N-(2,4-dimethoxybenzyl)-4-fluoro-N-1,2,4-thiadiazol-5-ylbenzenesulfonamide (Preparation 1, 0.248 g, 0.571 mmol) was added to the reaction mixture portion-wise and the mixture stirred under a nitrogen atmosphere at ambient temperature for 2 hours. The reaction was quenched with a 1M aqueous solution of sodium hydroxide (100 mL) and extracted with ethyl acetate (3×100 mL). The organic layer was separated and washed with water (100 mL), dried over MgSO$_4$, filtered and concentrated in vacuo to give a yellow oil. The oil was purified by silica gel column chromatography (ethyl acetate elution) to afford the title compound (0.295 g, 93%) and this was used without further purification.

The following Preparations were carried out according to Processes D or F, employing the appropriate thiol of formula (III) and 2,4-dimethoxybenzyl derivative of formula (IV).

Preparation 16

3-Cyano-N-(2,4-dimethoxybenzyl)-4-[(4-methoxyphenyl)thio]-N-1,2,4-thiadiazol-5-ylbenzenesulfonamide

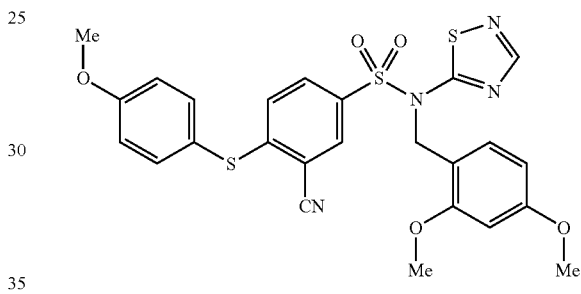

3-Cyano-N-(2,4-dimethoxybenzyl)-4-fluoro-N-1,2,4-thiadiazol-5-ylbenzenesulfonamide (Preparation 1, 0.100 g, 0.230 mmol) and potassium carbonate (0.0668 g, 0.483 mmol) were stirred in N,N-dimethylacetamide (3 mL). 4-Methoxythiophenol (0.0322 g, 0.230 mmol) was added to the reaction mixture and stirred under a nitrogen atmosphere at ambient temperature overnight. The reaction mixture was partitioned between ethyl acetate and water. The organic layer was separated and washed with a 1M aqueous solution of sodium hydroxide, then brine (×3). The organic layer was dried, filtered and concentrated in vacuo to afford the title compound as a solid (0.13 g, 100%), which was used without purification.

| Pr | Name | Data | Method |
|---|---|---|---|
| 13 | 3-cyano-N-(2,4-dimethoxybenzyl)-4-[(2-fluorophenyl)thio]-N-1,2,4-thiadiazol-5-ylbenzenesulfonamide | LCMS Rt = 2.47 min MS m/z no mass ion observed | D |
| 14 | 3-cyano-N-(2,4-dimethoxybenzyl)-N-1,2,4-thiadiazol-5-yl-4-{[3-(trifluoromethyl)phenyl]thio}benzenesulfonamide | LCMS Rt = 4.39 min MS m/z 590.9 [MH]– | F |
| 15 | 3-cyano-N-(2,4-dimethoxybenzyl)-N-1,2,4-thiadiazol-5-yl-4-{[4-(trifluoromethyl)phenyl]thio}benzenesulfonamide | LCMS Rt = 4.47 min MS m/z 590.9 [MH]– | F |

Preparation 17

3-Cyano-N-(2,4-dimethoxybenzyl)-4-[(3-methoxyphenyl)thio]-N-1,2,4-thiadiazol-5-ylbenzenesulfonamide

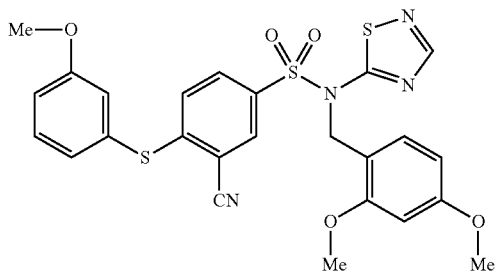 [SMILES: COc1cccc(Sc2ccc(S(=O)(=O)N(Cc3ccc(OC)cc3OC)c3ncns3)cc2C#N)c1]

3-Methoxythiophenol (0.0801 g, 0.571 mmol) and potassium carbonate (0.158 g, 1.14 mmol) were stirred in dimethylsulphoxide. 3-Cyano-N-(2,4-dimethoxybenzyl)-4-fluoro-N-1,2,4-thiadiazol-5-ylbenzenesulfonamide (Preparation 1, 0.248 g, 0.571 mmol) was added to the reaction mixture and the mixture stirred at 50° C. overnight. The reaction mixture was partitioned between ethyl acetate and water. A 1M aqueous solution of sodium hydroxide was added to the mixture. The organic layer was separated and dried over $MgSO_4$, filtered and concentrated in vacuo to afford a white solid. The solid was triturated in ethyl acetate and filtered to afford the title compound (0.204 g, 64%).

$^1$HNMR ($CD_3OD$): δ 3.59 (s, 3H), 3.72 (s, 3H), 3.79 (s, 3H), 5.18 (s, 2H), 6.37-6.42 (m, 2H), 6.90-6.97 (m, 2H), 7.12-7.19 (m, 3H), 7.45-7.50 (m, 1H), 7.86-7.90 (m, 1H), 8.06 (s, 1H), 8.38 (s, 1H).

Preparation 18

N-(2,4-Dimethoxy-benzyl)-[1,2,4]thiadiazol-5-yl-amine/N-(2,4-dimethoxybenzyl)-1,2,4-thiadiazol-5-amine

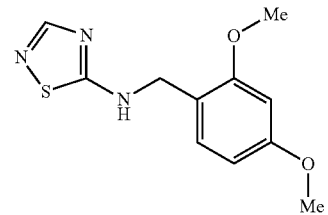 [SMILES: COc1ccc(CNc2ncns2)c(OC)c1]

A mixture of 5-amino-1,2,4-thiadiazole (1 g, 9.89 mmol) and 2,4-dimethoxybenzaldehyde (1.81 g, 10.9 mmol) in toluene (30 mL) was refluxed under Dean-Stark conditions for 2 hours. The reaction mixture was evaporated and the residue taken up in methanol (25 mL), $NaBH_4$ (600 mg, 15.9 mmol) was added carefully in small portions (vigorous effervescence after each addition), and the reaction was left stirring overnight at ambient temperature. Aqueous HCl (2M, 1 mL) was added followed by aqueous NaOH (2M, 10 mL). The bulk of the methanol was evaporated, water (20 mL) added and extracted with ethyl acetate (2×30 mL). The combined organic was washed brine (20 mL), dried, and evaporated. The residue was purified by silica gel column chromatography (ISCO™ column 120 g; 25%-60% ethyl acetate in heptane gradient elution) to furnish a semi-solid residue that was re-evaporated from heptane. tert-Butylmethyl ether (2-3 mL) was added, followed by heptane (2-3 mL). The resulting solid was collected by filtration, washed with heptane and dried to afford the title compound (1.22 g, 49%).

$^1$HNMR ($d_6$-DMSO): δ 3.73 (s, 3H), 3.78 (s, 3H), 4.36 (d, 2H), 6.47 (dd, 2.34 Hz, 1H), 6.56 (d, 1H), 7.15 (d, 1H), 7.88 (s, 1H), 8.65 (br s, 1H)

Preparation 19

N-(2,4-Dimethoxybenzyl)-1,3,4-thiadiazol-2-amine

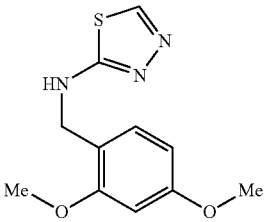 [SMILES: COc1ccc(CNc2nncs2)c(OC)c1]

To a solution of 2-amino-1,3,4-thiadiazole (3.05 g, 30.2 mmol) and 2,4-dimethoxybenzaldehyde (4.55 g, 27.4 mmol) in dichloromethane (125 mL) was added chlorotriisopropoxytitanium (16 mL, 67.0 mmol) portion-wise over 5 minutes. After stirring for 1 hour, sodium triacetoxyborohydride (11.72 g, 55.3 mmol) was added portion-wise and stirred for 24 hours. The reaction was quenched with saturated aqueous sodium bicarbonate solution, adjusted to pH 9 with aqueous sodium hydroxide (6 N solution) and extracted with dichloromethane. The combined organic extracts were dried over anhydrous magnesium sulfate, filtered and concentrated in vacuo. The residue was purified by silica gel flash column chromatography (0-10% methanol in dichloromethane gradient elution) to afford the title compound as a white solid (0.590 g, 86%).

$^1$HNMR ($d_6$-DMSO): δ 3.75 (s, 3H), 3.80 (s, 3H), 4.37 (d, 2H), 6.49 (m, 1H), 6.58 (s, 1H), 7.19 (d, 1H), 7.97 (m, 1H), 8.59 (s, 1H).

LCMS Rt=1.36 min MS m/z 252 [MNa]+

Preparation 20

4-Bromopyridazine hydrobromide

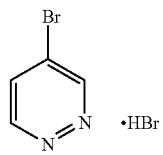

3-Bromofuran (5.0 g, 34.0 mmol) and potassium acetate (9.2 g, 93.7 mmol) were suspended in acetic acid (30 mL). Bromine (1.75 mL, 34.2 mmol) in acetic acid (10 mL) was added dropwise. The reaction mixture was then stirred for one hour. The reaction mixture was filtered and the filtrate concentrated in vacuo. The residue was dissolved in ethanol (50 mL) and hydrazine hydrate (5 mL, 103 mmol) was added dropwise to the solution, which was then stirred at room temperature for two hours. The reaction was diluted in ethyl acetate (100 mL) and a solution of saturated aqueous brine (100 mL). The organic layer was collected and washed once more with a solution of saturated aqueous brine (100 mL). The aqueous layer was extracted with ethyl acetate (50 mL). The organic layers were combined, then dried over sodium sulfate, filtered, and concentrated in vacuo. The resulting residue was dissolved in 1,4-dioxane (25 mL) and hydrobromic acid in acetic acid (5 mL) was added dropwise. The resulting brown solid was filtered, then suspended in acetone (25 mL), subjected to a sonication bath and finally filtered again. The title compound was isolated as a brown solid (5.95 g, 73% yield).
$^{1}$HNMR (d$_{6}$-DMSO): δ 8.10 (m, 1H), 7.80-8.80 (br s, 1H), 9.10 (d, 1H), 9.45 (s, 1H)
LCMS Rt=0.75 min MS m/z 159 [MH]+

Preparation 21

4-[2-Chloro-5-(trifluoromethyl)phenyl]pyridazine

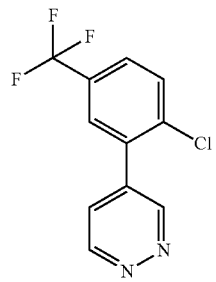 [SMILES: FC(F)(F)c1ccc(Cl)c(-c2ccnnc2)c1]

[2-Chloro-5-(trifluoromethyl)phenyl]boronic acid (0.410 g, 1.83 mmol), caesium carbonate (1.1 g, 3.38 mmol) and 4-bromopyridazine hydrobromide (Preparation 20, 0.35 g, 1.46 mmol) were dissolved in 1,4-dioxane (3.5 mL) and water (1 mL). The mixture was heated to 80° C. under nitrogen then palladium tetrakis triphenylphosphine (0.085 g, 0.074 mmol) was added. The reaction was stirred for three hours before it was left to cool to room temperature. The mixture was subsequently filtered through Arbocel®, then diluted in ethyl acetate (15 mL) and washed twice with a saturated solution of aqueous brine (15 mL). The organic layer was collected, dried over sodium sulphate, filtered and concentrated in vacuo. The residue was purified by silica gel column chromatography (ISCO™, 0-50% ethyl acetate in heptane gradient elution, 12 g SiO$_{2}$) to give title compound as a green solid (0.23 g, 61%).
$^{1}$HNMR (d$_{6}$-DMSO): δ 7.90 (m, 3H), 8.00 (s, 1H), 9.35 (d, 1H), 9.41 (s, 1H)
LCMS Rt=1.47 min MS m/z 259.2 [MH]$^{+}$ Preparation 22

3-Cyano-N-(2,4-dimethoxybenzyl)-4-{[2-pyridazin-4-yl-4-(trifluoromethyl)phenyl]thio}-N-1,2,4-thiadiazol-5ylbenzenesulfonamide

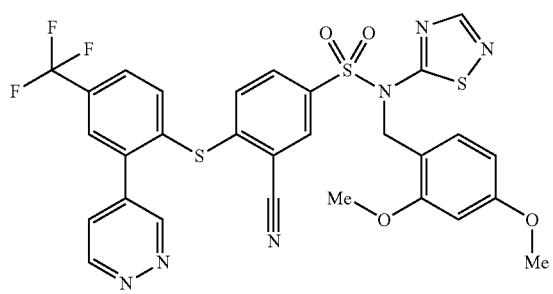 [SMILES: COc1ccc(CN(c2ncns2)S(=O)(=O)c2ccc(Sc3ccc(C(F)(F)F)cc3-c3ccnnc3)c(C#N)c2)c(OC)c1]

4-[2-Chloro-5-(trifluoromethyl)phenyl]pyridazine (Preparation 21, 0.050 g, 0.193 mmol), triisopropylsilanethiol (0.090 g, 472 mmol) and potassium carbonate (0.055 g, 0.398 mmol) were dissolved in N,N-dimethylacetamide (2 mL) in a Reactivial®. The reaction mixture was heated to 130° C. for 1 hour and 15 minutes. Then, the reaction was cooled to room temperature and 3-cyano-N-(2,4-dimethoxybenzyl)-4-fluoro-N-1,2,4-thiadiazol-5-ylbenzenesulfonamide (Preparation 1, 0.085 g, 1.96 mmol) was added. The mixture was stirred at room temperature for thirty minutes. The reaction mixture was diluted in ethyl acetate (15 mL) and washed twice with a solution of saturated aqueous brine (15 mL). The aqueous layer was extracted with ethyl acetate (5 mL). The organic phases were combined and dried over sodium sulphate, filtered, and concentrated in vacuo. The residue was purified by silica gel column chromatography (ISCO™, 0-50% ethyl acetate in heptane gradient elution, 12 g SiO$_{2}$) to give title compound as a yellow foam (0.095 g, 73%).
$^{1}$HNMR (d$_{6}$-DMSO): δ 3.55 (s, 3H), 3.70 (s, 3H), 5.18 (s, 2H), 6.30 (s, 1H), 6.35 (d, 1H), 6.93 (d, 1H), 7.10 (d, 1H), 7.75 (m, 1H), 7.85-7.90 (m, 2H), 8.00 (m, 2H), 8.05 (s, 1H), 8.40 (s, 1H), 9.25 (d, 1H), 9.30 (s, 1H)
LCMS Rt=1.78 min MS m/z 671.1 [MH]$^{+}$ Preparation 23

5-Chloro-N-(2,4-dimethoxybenzyl)-2-fluoro-4-{[2-pyridazin-4-yl-4-(trifluoromethyl)phenyl]thio}-N-1,3,4-thiadiazol-2-ylbenzenesulfonamide

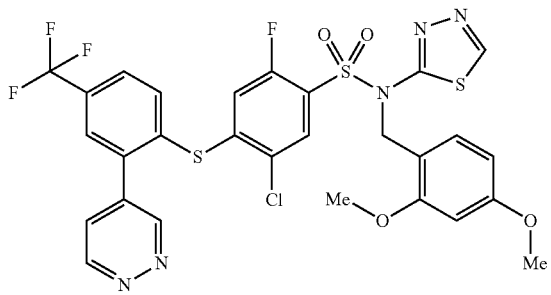 [SMILES: COc1ccc(CN(c2nncs2)S(=O)(=O)c2cc(Cl)c(Sc3ccc(C(F)(F)F)cc3-c3ccnnc3)cc2F)c(OC)c1]

Prepared according to Preparation 22 using 4-[2-chloro-5-(trifluoromethyl)phenyl]pyridazine (Preparation 21, 50 mg, 0.193 mmol) and 5-chloro-N-(2,4-dimethoxybenzyl)-2,4-difluoro-N-1,3,4-thiadiazol-2-ylbenzenesulfonamide (Preparation 2, 95 mg, 0.206 mmol). The residue was purified by silica gel column chromatography (ISCO™, 0-70% ethyl acetate in heptane gradient elution, 12 g SiO$_{2}$) to give title compound as an off-white solid (0.095 g, 71%).
$^{1}$HNMR (d$_{6}$-DMSO): δ 3.60 (s, 3H), 3.70 (s, 3H), 5.10 (s, 2H), 6.35-6.40 (m, 2H), 6.95 (d, 1H), 7.08 (d, 1H), 7.65 (d, 1H), 7.80 (m, 1H), 7.90 (d, 1H), 8.00 (m, 1H), 8.02 (s, 1H), 9.30 (m, 2H), 9.35 (s, 1H)
LCMS Rt=1.76 min MS m/z 698.1 [MH]$^{+}$ Preparation 24 tert-Butyl[4-(4,4,5,5-tetramethyl-1,3,2-dioxaborolan-2-yl)pyridin-2-yl]carbamate

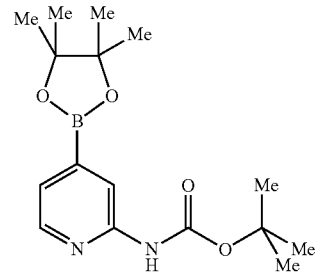 [SMILES: CC(C)(C)OC(=O)Nc1cc(B2OC(C)(C)C(C)(C)O2)ccn1]

tert-Butyl (4-bromopyridin-2-yl)carbamate (0.494 g, 1.81 mmol), bis(pinacolato)diboron (1.4 g 5.51 mmol) and potassium acetate (0.535 g, 5.45 mmol) were stirred in dimethylsulfoxide (8 mL). The mixture was flushed with nitrogen for 10 minutes. [1,1-Bis(diphenylphosphino)ferrocene]dichloropalladium(II) (0.150 g, 0.184 mmol) was added and the system flushed for a further 5 minutes with nitrogen before heating the reaction mixture to 85° C. under nitrogen for 1 hour. The reaction mixture was diluted in ethyl acetate (15 mL) and washed with aqueous hydrochloride solution (10 mL, 0.2 M). Some of the product went into the aqueous layer and some stayed in the organic layer. The aqueous layer was treated with saturated aqueous sodium carbonate carefully until ~pH 6 was achieved then extracted with ethyl acetate (10 mL). The organics were dried over sodium sulfate, filtered and concentrated in vacuo to give title compound as a white solid (0.44 g, 76%).

$^1$HNMR (d$_6$-DMSO): δ 1.29 (s, 12H), 1.45 (s, 9H), 7.15-7.17 (d, 1H), 8.07 (s, 1H), 8.24-8.25 (d, 1H), 9.77 (s, 1H)

LCMS Rt=0.68 min MS m/z 183.1 [MH]$^+$

Preparation 25 tert-Butyl{4-[2-fluoro-5-(trifluoromethyl)phenyl]pyridin-2-yl}carbamate

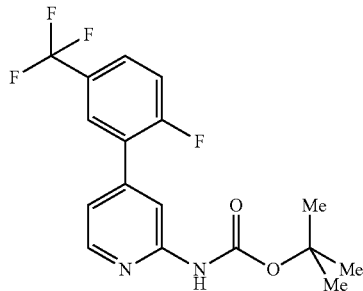 [SMILES: CC(C)(C)OC(=O)Nc1cc(-c2cc(C(F)(F)F)ccc2F)ccn1]

Prepared according to Preparation 21 using 1-fluoro-2-iodo-4-(trifluoromethyl)benzene and tert-butyl[4-(4,4,5,5-tetramethyl-1,3,2-dioxaborolan-2-yl)pyridin-2-yl]carbamate (Preparation 24, 430 mg, 1.0 mmol). The residue was purified by silica gel column chromatography (ISCO™, 0-30% ethyl acetate in heptane gradient elution, 2×12 g SiO$_2$) to give title compound as a green solid (0.105 g, 41%).

$^1$HNMR (d$_6$-DMSO): δ 7.90 1.45 (s, 9H), 7.25 (m, 1H), 7.59-7.64 (t, 1H), 7.89-7.93 (m, 2H), 7.98 (d, 1H), 8.35 (d, 1H), 9.96 (s, 1H)

LCMS Rt=1.80 min MS m/z 357.1 [MH]$^+$

Preparation 26

4-{[2-(2-Aminopyridin-4-yl)-4-(trifluoromethyl)phenyl]thio}-5-chloro-N-(2,4-dimethoxybenzyl)-2-fluoro-N-1,3,4-thiadiazol-2-ylbenzenesulfonamide

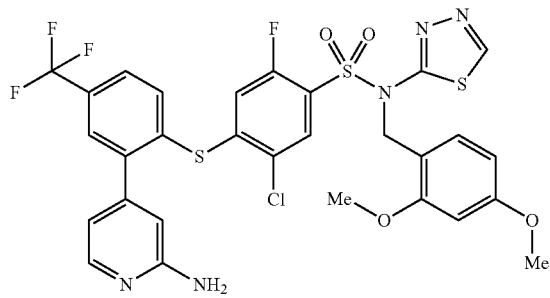 [SMILES: COc1ccc(CN(c2nncs2)S(=O)(=O)c2cc(Cl)c(Sc3ccc(C(F)(F)F)cc3-c3ccnc(N)c3)cc2F)c(OC)c1]

Prepared according to Preparation 22 using tert-butyl{4-[2-fluoro-5-(trifluoromethyl)phenyl]pyridin-2-yl}carbamate (Preparation 25, 100 mg, 0.24 mmol) and 5-chloro-N-(2,4-dimethoxybenzyl)-2,4-difluoro-N-1,3,4-thiadiazol-2-ylbenzenesulfonamide (Preparation 2, 110 mg, 0.24 mmol). The residue was purified by silica gel column chromatography (ISCO™, 0-40% ethyl acetate in heptane gradient elution, 12 g SiO$_2$) to give title compound as yellow oil (0.153 g, 90%).

$^1$HNMR (d$_6$-DMSO): δ 3.60 (s, 3H), 3.66 (s, 3H), 5.10 (s, 2H), 6.07 (s, 2H), 6.34 (m, 1H), 6.37-6.39 (m, 2H), 6.46 (dd, 1H), 6.90 (d, 1H), 7.06 (d, 1H), 7.66 (d, 1H), 7.73 (m, 2H), 7.84-7.87 (m, 1H), 7.90 (d, 1H), 9.29 (s, 1H).

LCMS Rt=2.01 min MS m/z 712.1 [MH]$^+$

Preparation 27

4-Bromo-3-cyanobenzenesulfonyl chloride

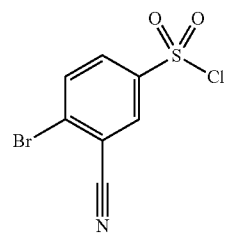 [SMILES: N#Cc1cc(S(=O)(=O)Cl)ccc1Br]

To a solution of 5-amino-2-bromo benzonitrile (10.0 g, 50.75 mmol) in concentrated hydrogen chloride (25 mL) and acetic acid (25 mL) was added sodium nitrite (3.85 g, 55.82 mmol) in water (12.5 mL). The reaction was stirred at 0° C. for 15 minutes. In a separate flask was prepared a saturated solution of sulfur dioxide in acetic acid (25 mL) at 0° C. Calcium chloride dihydrate (3.46 g, 20.30 mmol) was added to the saturated solution prior to the dropwise addition of the solution containing 5-amino-2-bromo benzonitrile. The reaction mixture was warmed to room temperature and stirred for 16 hours. The reaction mixture was diluted with water and the resulting white precipitate collected by filtration. The solids were dissolved in dichloromethane and washed with a saturated aqueous solution of sodium chloride. The organics were dried over anhydrous sodium sulfate, filtered and concentrated in vacuo. The material was purified by column chromatography (5% ethyl acetate in heptane elution). Fractions containing product were combined and concentrated in vacuo to obtain the title compound as a colourless solid.

$^1$HNMR (CDCl$_3$): δ 7.98-8.00 (d, 1H), 8.06-8.09 (dd, 1H), 8.28 (s, 1H)

LCMS Rt=1.78 min MS m/z 343 [MH(—C$_9$H$_{10}$O$_2$)]—

Preparation 28

4-Bromo-3-cyano-N-(2,4-dimethoxybenzyl)-N-1,2,4-thiadiazol-5-ylbenzenesulfonamide

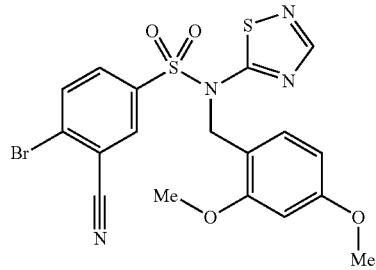 [SMILES: COc1ccc(CN(c2ncns2)S(=O)(=O)c2ccc(Br)c(C#N)c2)c(OC)c1]

To a nitrogen purged solution of N-(2,4-dimethoxybenzyl)-1,2,4-thiadiazol-5-amine (Preparation 18, 448 mg, 1.78 mmol) in tetrahydrofuran (7.5 mL) at −78° C. was added lithium hexamethyl disilazane (1.0 M in tetrahydrofuran, 1.96 mL). The reaction was stirred for 15 minutes before a solution of 4-bromo-3-cyanobenzenesulfonyl chloride (Preparation 27, 500 mg, 1.78 mmol) in tetrahydrofuran (7.5 mL) was added dropwise. The reaction mixture was warmed to room temperature and stirred for 3 hours. The reaction mixture was partitioned between water (10 mL) and ethyl acetate (3×10 mL). The combined organic extracts were washed with a saturated aqueous solution of sodium chloride, dried over anhydrous sodium sulfate, filtered and concentrated in vacuo to afford a yellow solid. The material was purified by silica gel column chromatography (ISCO™ companion, 40 g column, 0-30% ethyl acetate in heptane gradient elution). Fractions containing product were combined and concentrated in vacuo to obtain the title compound as a colourless solid (883 mg, 73%)

$^1$HNMR (d$_6$-DMSO): δ 3.62 (s, 3H), 3.74 (s, 3H), 5.24 (s, 2H), 6.38 (d, 1H), 6.42 (dd, 1H), 7.02 (d, 1H), 7.97-8.02 (m, 1H), 8.03-8.08 (m, 1H), 8.16-8.18 (m, 1H), 8.45 (s, 1H).

LCMS Rt=1.78 min MS m/z 343 [MH(—C$_9$H$_{10}$O$_2$)]—

Preparation 29

3-Cyano-N-(2,4-dimethoxybenzyl)-4-(5,5-dimethyl-1,3,2-dioxaborinan-2-yl)-N-1,2,4-thiadiazol-5-ylbenzenesulfonamide

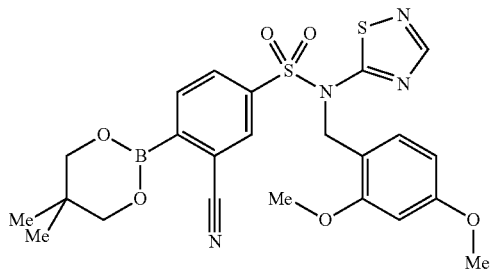 [SMILES: COc1ccc(CN(c2ncns2)S(=O)(=O)c2ccc(B3OCC(C)(C)CO3)c(C#N)c2)c(OC)c1]

To a solution of 4-bromo-3-cyano-N-(2,4-dimethoxybenzyl)-N-1,2,4-thiadiazol-5-ylbenzenesulfonamide (Preparation 28, 500 mg, 1.01 mmol) in tetrahydrofuran (10 mL) was added bis(neopentylgylcolato)diboron (239 mg, 1.06 mmol), potassium acetate (297 mg, 3.03 mmol) and bis(diphenylphosphino)ferrocene palladium (II) chloride, dichloromethane complex (41 mg, 0.05 mmol). The reaction mixture was heated to reflux and stirred for 6 hours. The reaction mixture was concentrated in vacuo and partitioned between water (10 mL) and ethyl acetate (20 mL). The organic extracts were washed with a saturated aqueous solution of sodium chloride (5 mL), dried over anhydrous magnesium sulfate, filtered and concentrated in vacuo to afford the title compound as a brown foam (572 mg), which was used without further purification.

$^1$HNMR (CDCl$_3$): δ 1.05 (s, 6H), 3.64 (s, 3H), 3.79 (s, 3H), 3.84 (s, 4H), 5.30 (s, 2H), 6.22-6.23 (dd, 1H), 6.33-6.35 (dd, 1H), 7.07-7.09 (d, 1H), 7.81 (m, 1H), 7.86-7.92 (m, 2H), 8.21 (s, 1H).

LCMS Rt=1.58 min MS m/z 459 [MH (—C$_5$H$_8$)]—

Preparation 30

3-Cyano-N-(2,4-dimethoxybenzyl)-4-[2-methoxy-4-(trifluoromethyl)benzyl]-N-1,2,4-thiadiazol-5-ylbenzenesulfonamide

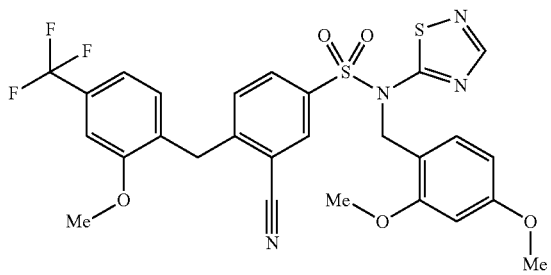 [SMILES: COc1ccc(CN(c2ncns2)S(=O)(=O)c2ccc(Cc3ccc(C(F)(F)F)cc3OC)c(C#N)c2)c(OC)c1]

To a solution of 3-cyano-N-(2,4-dimethoxybenzyl)-4-(5,5-dimethyl-1,3,2-dioxaborinan-2-yl)-N-1,2,4-thiadiazol-5-ylbenzenesulfonamide (Preparation 29, 45.5 mg, 0.086 mmol) in tetrahydrofuran (1 mL) was added a 2 M aqueous solution of potassium carbonate (116 µL, 3.03 mmol) and 2-methoxy-4-(trifluoromethyl)benzyl bromide (21 mg, 0.08 mmol). The solution was sparged with nitrogen before the addition of tetrakis(triphenylphosphine)palladium (0) (9.2 mg, 0.0008 mmol). The reaction mixture was heated at 65° C. for 6 hours. The reaction mixture was cooled to ambient temperature and partitioned between 1N aqueous citric acid solution (2 mL) and ethyl acetate (10 mL). The organic layer was washed with a saturated aqueous solution of sodium chloride (2 mL), dried over anhydrous magnesium sulphate, filtered and concentrated in vacuo to give a yellow oil. The material was purified by silica gel column chromatography (ISCO™ companion, 12 g column, 0-50% ethyl acetate in heptane gradient elution). Fractions containing product were combined and concentrated in vacuo to obtain the title compound as a yellow oil, which was used without further purification.

$^1$HNMR (CDCl$_3$): δ 3.55 (s, 3H), 3.79 (s, 3H), 3.87 (s, 3H), 4.21 (s, 2H), 5.30 (s, 2H), 6.14-6.15 (d, 1H), 6.33-6.35 (dd, 1H), 7.08-7.10 (m, 2H), 7.23-7.32 (m, 3H), 7.73-7.74 (m, 1H), 7.78-7.80 (m, 1H), 8.20 (s, 1H).

LCMS Rt=1.98 min MS m/z 603 [MH]−

Preparation 31

Ethyl 2-pyridazin-4-yl-4-(trifluoromethyl)benzoate

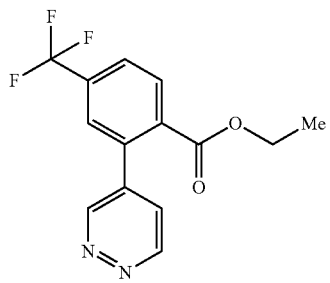 [SMILES: CCOC(=O)c1ccc(C(F)(F)F)cc1-c1ccnnc1]

To a solution of 2-iodo-4-trifluoromethylbenzoic acid ethyl ester (200 mg, 0.581 mmol) in acetonitrile (5 mL) was added 4-(tributylstannyl)pyridazine (214 mg, 0.581 mmol) and caesium fluoride (176 mg, 1.16 mmol). The solution was sparged with nitrogen before the addition of tetrakis(triphenylphosphine)palladium (0) (26 mg, 0.023 mmol) and copper iodide (22 mg, 0.116 mmol). The reaction mixture was sparged with nitrogen then heated at 45° C. for 2 hours. The reaction mixture was cooled to ambient temperature, diluted with ethyl acetate and filtered through Celite™. An aqueous solution of potassium fluoride was added and the reaction mixture was stirred for 16 hours. The organic layer was separated, washed with water, followed by a saturated aqueous solution of sodium chloride. The organic layer was dried over anhydrous sodium sulphate, filtered and concentrated in vacuo. The material was purified by column chromatography (100-200 silica, eluting with 60% ethyl acetate in heptane). Fractions containing product were combined and concentrated in vacuo to obtain the title compound as a solid (140 mg).

$^1$HNMR (CDCl$_3$): δ 1.09 (t, 3H), 4.18 (q, 2H), 7.45 (s, 1H), 7.57 (s, 1H), 7.82 (d, 1H), 8.17 (d, 1H), 9.14 (s, 1H), 9.26 (s, 1H).

LCMS Rt=3.25 min MS m/z 297 [MH]+

Preparation 32

[2-Pyridazin-4-yl-4-(trifluoromethyl)phenyl]methanol

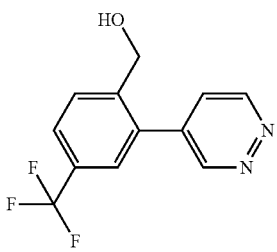 [SMILES: OCc1ccc(C(F)(F)F)cc1-c1ccnnc1]

To a solution of ethyl 2-pyridazin-4-yl-4-(trifluoromethyl) benzoate (Preparation 31, 510 mg, 1.72 mmol) in tetrahydrofuran (15 mL) cooled to 0° C. was added lithium aluminium hydride (2.0 M in tetrahydrofuran, 0.86 mL, 1.72 mmol) dropwise. The reaction was stirred for 1 hour at 0° C. before warming to room temperature and stirring for a further 2 hours. The reaction was re-cooled to 0° C. before excess lithium aluminium hydride was quenched by the addition of water (65 μL), 2M aqueous solution of sodium hydroxide (130 μL) and further water (195 μL). Diethyl ether and anhydrous magnesium sulphate were added to aid the formation of a granular solid which was filtered. The organics were concentrated in vacuo and re-dissolved in dichloromethane (5 mL). The organics were purified by silica gel column chromatography (ISCO™ companion, 40 g column, eluting with 100% heptane to 100% ethyl acetate to 5% methanol in ethyl acetate). Fractions containing product were combined and concentrated in vacuo to obtain the title compound as a yellow solid (197 mg, 45%).

$^1$HNMR (CDCl$_3$): δ 4.67 (s, 2H), 7.56 (s, 1H), 7.62-7.64 (m, 1H), 7.77-7.82 (m, 2H), 9.31 (s, 2H).

LCMS Rt=1.25 min MS m/z 255 [MH]+

Preparation 33

4-[2-(Bromomethyl)-5-(trifluoromethyl)phenyl]pyridazine

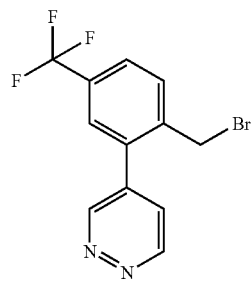 [SMILES: FC(F)(F)c1ccc(CBr)c(-c2ccnnc2)c1]

[2-Pyridazin-4-yl-4-(trifluoromethyl)phenyl]methanol (Preparation 32, 46 mg, 0.18 mmol) was dissolved in dichloromethane (2 mL) and cooled to 0° C. Phosphorus tribromide (1.0 M in dichloromethane, 199 μL, 0.20 mmol) was added and the reaction stirred for 30 minutes. Water (2 mL) was added dropwise to the reaction at 0° C. before the organics were separated and dried using a phase separation cartridge. The organics were concentrated in vacuo to afford the title compound as a residue which was re-dissolved in THF (1 mL) and used without further purification.

LCMS Rt=1.49 min MS m/z 319 [M$^{81}$BrH]+

Preparation 34

3-Cyano-N-(2,4-dimethoxybenzyl)-4-[2-pyridazin-4-yl-4-(trifluoromethyl)benzyl]-N-1,2,4-thiadiazol-5-ylbenzenesulfonamide

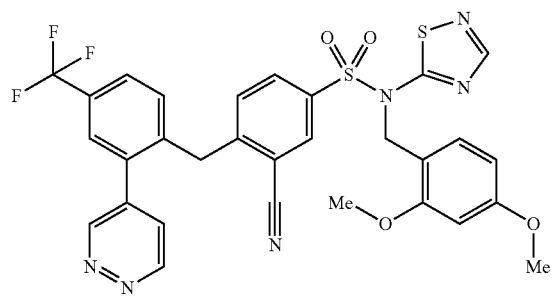 [SMILES: COc1ccc(CN(c2ncns2)S(=O)(=O)c2ccc(Cc3ccc(C(F)(F)F)cc3-c3ccnnc3)c(C#N)c2)c(OC)c1]

To a solution of 3-cyano-N-(2,4-dimethoxybenzyl)-4-(5,5-dimethyl-1,3,2-dioxaborinan-2-yl)-N-1,2,4-thiadiazol-5-ylbenzenesulfonamide (Preparation 29, 100 mg, 0.19 mmol) in tetrahydrofuran (2 mL) was added a 2 M aqueous solution of potassium carbonate (270 μL, 0.54 mmol) and 4-[2-(bromomethyl)-5-(trifluoromethyl)phenyl]pyridazine (Preparation 33, 57 mg, 0.18 mmol). The solution was sparged with nitrogen before the addition of tetrakis(triphenylphosphine) palladium (0) (20.8 mg, 0.018 mmol). The reaction mixture was heated at 65° C. for 6 hours. The reaction mixture was cooled to ambient temperature and partitioned between a saturated aqueous solution of ammonium chloride (5 mL) and ethyl acetate (2×10 mL). A saturated aqueous solution of sodium chloride was added to aid the separation. The combined organic layer was dried over anhydrous magnesium sulphate, filtered and concentrated in vacuo to give a brown oil. The material was purified by silica gel column chromatography (ISCO™ companion, 12 g column, 0-30% ethyl acetate in heptane gradient elution). Fractions containing product were combined and concentrated in vacuo to obtain the title compound as a foam.

LCMS Rt=1.80 min MS m/z 653 [MH]+, 651 [MH]−

Preparation 35

3-Cyano-N-(2,4-dimethoxybenzyl)-4-[(2-methoxy-4-(trifluoromethyl)phenyl)thio]-N-1,2,4-thiadiazol-5-ylbenzenesulfonamide

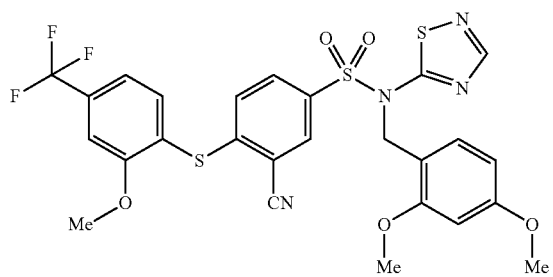 [SMILES: COc1ccc(CN(c2ncns2)S(=O)(=O)c2ccc(Sc3ccc(C(F)(F)F)cc3OC)c(C#N)c2)c(OC)c1]

Prepared according to Preparation 22 using 2-fluoro-5-(trifluoromethyl)anisole (500 mg, 2.57 mmol) and 3-cyano-N-(2,4-dimethoxybenzyl)-4-fluoro-N-1,2,4-thiadiazol-5-yl-benzenesulfonamide (Preparation 1, 880 mg, 2.57 mmol). Material was purified by silica gel column chromatography (33% ethyl acetate in heptane) to afford the title compound as a white solid (48 mg, 6%).

$^1$HNMR (CDCl$_3$): δ 3.61 (s, 3H), 3.80 (s, 3H), 3.87 (s, 3H), 5.29 (s, 2H), 6.23 (s, 1H), 6.34 (m, 1H), 6.78 (m, 1H), 7.03 (m, 1H), 7.20 (m, 1H), 7.30 (m, 1H), 7.60 (m, 2H), 7.68 (m, 1H), 8.19 (s, 1H).

LCMS Rt=4.36 min MS m/z 622 [MH]+

Preparation 36

4-{[2-(2-Aminopyridin-4-yl)-4-(trifluoromethyl)phenyl]thio}-5-chloro-2-fluoro-N-(2,4-dimethoxy-benzyl)-pyrimidin-2-ylbenzenesulfonamide

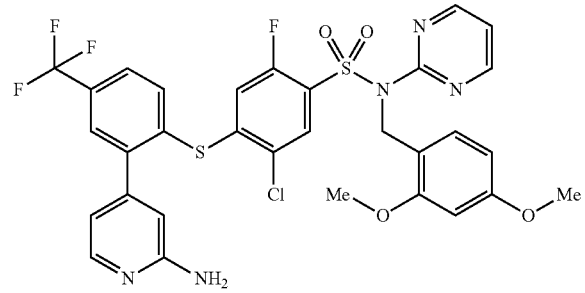 [SMILES: COc1ccc(CN(c2ncccn2)S(=O)(=O)c2cc(Cl)c(Sc3ccc(C(F)(F)F)cc3-c3ccnc(N)c3)cc2F)c(OC)c1]

Prepared according to Preparation 22 using tert-butyl{4-[2-fluoro-5-(trifluoromethyl)phenyl]pyridin-2-yl}carbamate (Preparation 25, 515 mg, 1.44 mmol) and 5-chloro-N-(2,4-dimethoxybenzyl)-2,4-difluoro-N-pyrimidin-2-yl-benzenesulfonamide (Preparation 37, 655 mg, 1.44 mmol). Material was purified by silica gel column chromatography (2-15% methanol in dichloromethane gradient elution) followed by a second silica gel column chromatography (0-10% methanol in ethyl acetate gradient elution) to afford the title compound (298 mg, 26%).

$^1$HNMR (CD$_3$OD): δ 3.66 (s, 3H), 3.72 (s, 3H), 5.31 (s, 2H), 6.38 (m, 1H), 6.47 (s, 1H), 6.51-6.56 (m, 2H), 6.67 (d, 1H), 7.03-7.09 (m, 2H), 7.68-7.73 (m, 2H), 7.77-7.83 (m, 3H), 8.43 (d, 2H).

LCMS Rt=2.71 min MS m/z 706 [MH]+

Preparation 37

5-Chloro-N-(2,4-dimethoxybenzyl)-2,4-difluoro-N-pyrimidin-2-yl-benzenesulfonamide

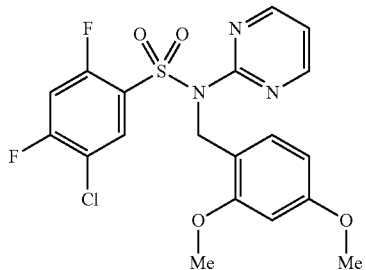 [SMILES: COc1ccc(CN(c2ncccn2)S(=O)(=O)c2cc(Cl)c(F)cc2F)c(OC)c1]

A solution of (2,4-dimethoxybenzyl)-pyrimidin-2-yl-amine (Preparation 38, 736 mg, 3 mmol) in anhydrous tetrahydrofuran (20 mL) was cooled to −78° C. before the addition of lithium(hexamethyldisilazane) (1M solution in tetrahydrofuran, 3.30 mL, 3.30 mmol). The reaction was allowed to warm to 0° C. for 30 minutes before cooling again to −78° C. The resulting solution was added to a solution of 3-chloro-4,6-difluorobenzenesulfonyl chloride (890 mg, 3.6 mmol) in tetrahydrofuran (10 mL) at −78° C. After 30 minutes at this temperature the reaction was warmed to room temperature and stirred for 24 hours. The reaction was quenched by the addition of saturated aqueous ammonium chloride solution and extracted into ethyl acetate. The organic layer was washed with brine, dried over magnesium sulfate and concentrated in vacuo. The residue was purified using silica gel column chromatography (50-100% dichloromethane in heptane gradient elution) to afford the title compound as a white solid (260 mg, 19%).

$^1$HNMR (d$_6$-DMSO): δ 3.73 (s, 3H), 3.75 (s, 3H), 5.27 (s, 2H), 6.47 (m, 1H), 6.57 (m, 1H), 7.01 (m, 1H), 7.18 (m, 1H), 7.82 (m, 1H), 8.10 (m, 1H), 8.57 (m, 2H).

LCMS Rt=1.77 min MS m/z 456 [MH]+

Preparation 38

(2,4-Dimethoxybenzyl)-pyrimidin-2-yl-amine

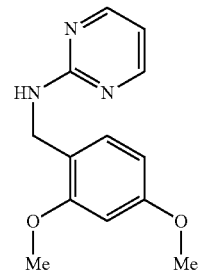 [SMILES: COc1ccc(CNc2ncccn2)c(OC)c1]

A mixture of 2-chloropyrimidine (1.37 g, 12 mmol), 2,4-dimethoxybenzylamine (2.61 g, 15.6 mmol) and triethylamine (2.51 mL, 18 mmol) in ethanol (8 mL) was heated in the microwave at 120° C. for 15 minutes. Water was added to the reaction mixture and the mixture extracted with dichloromethane (×3). The combined organic layers were washed with brine, dried over magnesium sulfate and concentrated in vacuo. The residue was purified using silica gel column chromatography (20-50% ethyl acetate in heptane gradient elution) to afford the title compound as a white solid (2.14 g, 72%).

$^1$HNMR (CD$_3$OD): δ 3.76 (s, 3H), 3.83 (s, 3H), 4.47 (s, 2H), 6.42 (m, 1H), 6.52 (m, 1H), 6.58 (m, 1H), 7.14 (m, 1H), 8.24 (m, 2H).

The ability of the compounds of formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 µg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 µg/ml G-418 in an incubator at 37° C. with a humidified atmosphere of 10% CO$_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM CaCl$_2$, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V½). Compounds were tested for their ability to inhibit hSCN9A sodium channels by activating the channel with a 20 msec voltage step to 0 mV following an 8 second conditioning prepulse to the empirically determined V½. Compound effect (% inhibition) was determined by difference in current amplitude before and after application of test compounds. For ease of comparison, "estimated IC-50" (EIC$_{50}$) values were calculated from single point electrophysiology data by the following equation, (tested concentration, uM)×(100-% inhibition/% inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of 1×10$^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V½ and current was activated by a 20 msec voltage step to 0 mV.

Electrophysiological assays may also be conducted using the Ionworks Quattro automated electrophysiological platform (Molecular Devices Corp). Intracellular and extracellular solutions were as described above with the following changes, 100 µg/ml amphotericin was added to the intracellular solution to perforate the membrane and allow electrical access to the cells. hSCN9A cells were grown and harvested as for PatchXpress and cells were resuspended in extracellular solution at a concentration of 3-4×10$^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assay described above using the PatchXpress platform and found to have the Nav1.7 EIC$_{50}$ (uM) values specified in the table below.

| Ex. | EIC$_{50}$ |
|---|---|
| 1 | 0.93 |
| 2 | 2.1 |
| 3 | 1.0 |
| 4 | 1.9 |
| 5 | 5.08 |

-continued

| Ex. | EIC$_{50}$ |
|---|---|
| 6 | 3.3 |
| 7 | 3.7 |
| 8 | 0.25 |
| 9 | 2.3 |
| 10 | 5.2 |
| 11 | >3 |
| 12 | 0.32 |
| 13 | 0.84 |
| 14 | 0.19 |
| 15 | 0.92 |
| 16 | 0.93 |
| 17 | 2.2 |
| 18 | 0.070 |
| 19 | 0.045 |
| 20 | 0.033 |
| 21 | 0.0058 |
| 22 | 0.14 |
| 23 | not tested |
| 24 | 0.072 |

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the EIC$_{50}$ value at the Nav1.7 channel to determine the selectivity of a given compound for Nav1.7 vs Nav1.5.

The invention claimed is:
1. A compound of formula (I):

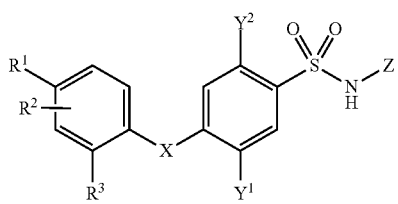

(I)

or a pharmaceutically acceptable salt thereof, wherein:
Z is a 'C-linked' 5- or 6-membered heteroaryl comprising (a) one or two nitrogen atoms or, when 5-membered, (b) one or two nitrogen atoms and one sulphur atom, said heteroaryl being optionally substituted on a ring carbon atom by F or Cl;
$Y^1$ is CN, F, Cl or $R^4$;
$Y^2$ is H or F;
X is $CH_2$ or S;
$R^1$ and $R^2$ are each independently H, Cl, F, $R^5$, Ar or Het$^1$;
$R^3$ is H, F, $R^5$, Ar or Het$^1$;
$R^4$ is ($C_1$-$C_4$)alkyl optionally substituted by one to three F;
$R^5$ is ($C_1$-$C_4$)alkyl, optionally substituted by one to three F; or ($C_1$-$C_4$)alkyloxy, optionally substituted by one to three F;
Ar is phenyl optionally substituted by one to three atoms or groups selected from the group consisting of Cl, F and $R^5$;
Het$^1$ is a 'C-linked' 5- or 6-membered heteroaryl group comprising one or two nitrogen atoms, being optionally substituted by one to three substituents selected from A or B;
A is attached to a Het$^1$ ring carbon and is selected from the group consisting of Het$^2$, $NH_2$ and $R^4$;
B is attached to a Het$^1$ ring nitrogen and is selected from the group consisting of 'C-linked' Het$^2$ and $R^4$; and
Het$^2$ is a 'C-linked' 3- to 8-membered saturated heterocyclic group comprising (a) one or two ring nitrogen atoms, or (b) one oxygen atom and one or two nitrogen atoms, said heterocyclic group being optionally substituted by $R^4$.

2. A compound according to claim 1 wherein X is S.
3. A compound according to claim 1 wherein X is $CH_2$.
4. A compound according to claim 1 wherein Z is either (a) a 'C-linked' 5-membered heteroaryl group containing two nitrogen atoms and one sulphur atom, or (b) a 'C-linked' 6-membered heteroaryl group containing two nitrogen atoms.
5. A compound according to claim 1 wherein Z is 'C-linked' thiadiazolyl or 'C-linked' pyrimidinyl.
6. A compound according to claim 1 wherein $Y^1$ is Cl and $Y^2$ is F.
7. A compound according to claim 1 wherein $Y^1$ is CN and $Y^2$ is H.
8. A compound according to claim 1 wherein $R^1$ and $R^2$ are independently H, F, Cl or $R^5$.
9. A compound according to claim 1 wherein $R^1$ and $R^2$ are independently H, F, $CF_3$ or $OCH_3$.
10. A compound according to claim 1 wherein $R^3$ is H, F, $R^5$ or Het$^1$.
11. A compound according to claim 1 wherein $R^3$ is H; F; ($C_1$-$C_4$)alkyl, optionally substituted by one to three F atoms; ($C_1$-$C_4$)alkyloxy; or a 'C-linked' 6-membered heteroaryl group comprising one or two nitrogen atoms, optionally substituted on a carbon atom by $NH_2$.
12. A pharmaceutical composition comprising a compound of formula (I) or a pharmaceutically acceptable salt thereof together, as defined in claim 1, with one or more pharmaceutically acceptable excipients.
13. A pharmaceutical composition according to claim 12 including one or more additional therapeutic agents.
14. A method for treating pain in a mammal, comprising administering to a mammal in need thereof a therapeutically effective amount of a compound of formula (I) or a pharmaceutically acceptable salt thereof, as defined in claim 1.
15. A method according to claim 14 in which said pain is selected from the group consisting of neuropathic, nociceptive and inflammatory pain.

* * * * *